United States Patent
Cho et al.

(10) Patent No.: US 8,039,634 B2
(45) Date of Patent: Oct. 18, 2011

(54) OXAZOLE HYDROXAMIC ACID DERIVATIVES AND USE THEREOF

(75) Inventors: Jeong-woo Cho, Daejeon (KR); Sang-chul Lim, Daejeon (KR); Cheol-young Maeng, Daejeon (KR); Sun-gwan Hwang, Daejeon (KR); Sung-jin Bae, Daejeon (KR); Eun-ae Kim, Daejeon (KR)

(73) Assignee: SK Holdings Co., Ltd., Seoul (KR)

( * ) Notice: Subject to any disclaimer, the term of this patent is extended or adjusted under 35 U.S.C. 154(b) by 724 days.

(21) Appl. No.: 11/795,303

(22) PCT Filed: Jan. 13, 2006

(86) PCT No.: PCT/KR2006/000140
§ 371 (c)(1), (2), (4) Date: Apr. 11, 2008

(87) PCT Pub. No.: WO2006/075888
PCT Pub. Date: Jul. 20, 2006

(65) Prior Publication Data
US 2009/0209596 A1   Aug. 20, 2009

(30) Foreign Application Priority Data

Jan. 14, 2005 (KR) .......... 10-2005-0003735
Jan. 10, 2006 (KR) .......... 10-2006-0002814

(51) Int. Cl.
C07D 213/16 (2006.01)
C07D 263/32 (2006.01)
(52) U.S. Cl. ............... 546/338; 548/235
(58) Field of Classification Search .......... 548/235
See application file for complete search history.

(56) References Cited

U.S. PATENT DOCUMENTS
6,432,999 B2 * 8/2002 Talley et al. .......... 514/406

FOREIGN PATENT DOCUMENTS
EP       1 787 986        5/2007
WO    WO 2005/040161    5/2005

OTHER PUBLICATIONS

Cancer and Metastasis Reviews (1998), 17(1), 91-106.*
Science (1999), vol. 286, 531-536.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Document 141:243543 retrieved from CAPLUS on Jun. 2010.*
Supplementary European Search Report.
Yujia Dai, et al., A Novel Series of Histone Deacetylase Inhibitors Incorporating Hetero Aromatic Ring Systems as Connection Units, vol. 13, 2003, pp. 3817-3820.
JP2004250401 A (Shizuoka Coffein Co. Ltd) Sep. 9, 2004 Example 43, Compound 115.
EP 526877 A2 (Bristol-Myers Squibb Company) Feb. 10, 1993 Claims 1-3, 6.
WO 9312075 A1 (Shionogi & Co., Ltd) Jun. 24, 1993—equivalent to USP 5,534,654.
International Search Report dated Apr. 21, 2006.

* cited by examiner

*Primary Examiner* — Shawquia Young

(57) ABSTRACT

Provided are an oxazole hydroxamic acid derivatives and pharmaceutically useful salt thereof as a histone deacetylase inhibitor. The oxazole hydroxamic acid derivative and pharmaceutically useful salt thereof, prepared in accordance with the present invention, can treat and/or prevent various cancers and inflammatory diseases caused by histone deacetylase.

4 Claims, 2 Drawing Sheets

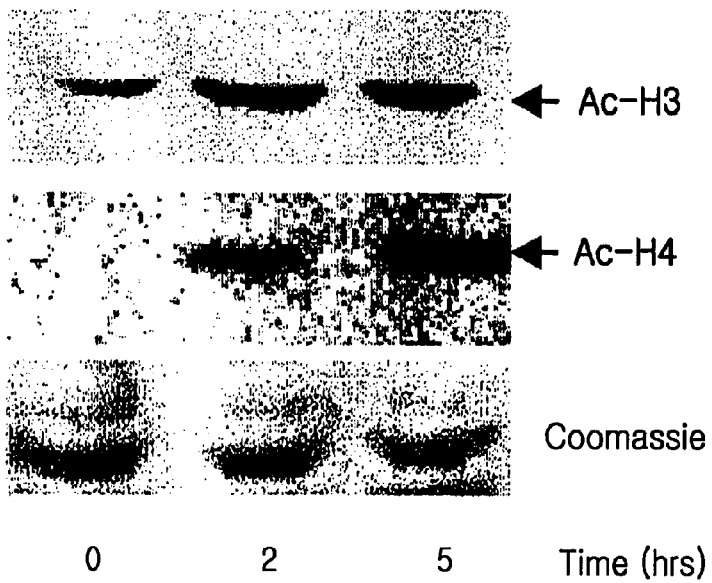
[Fig. 1]
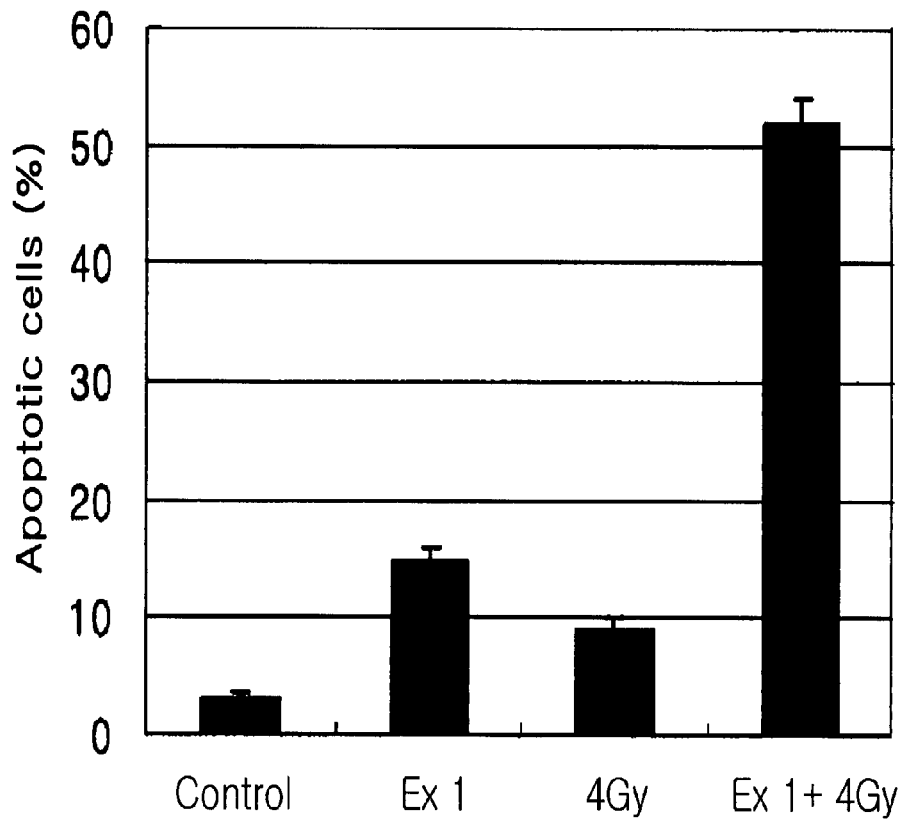
[Fig. 2]

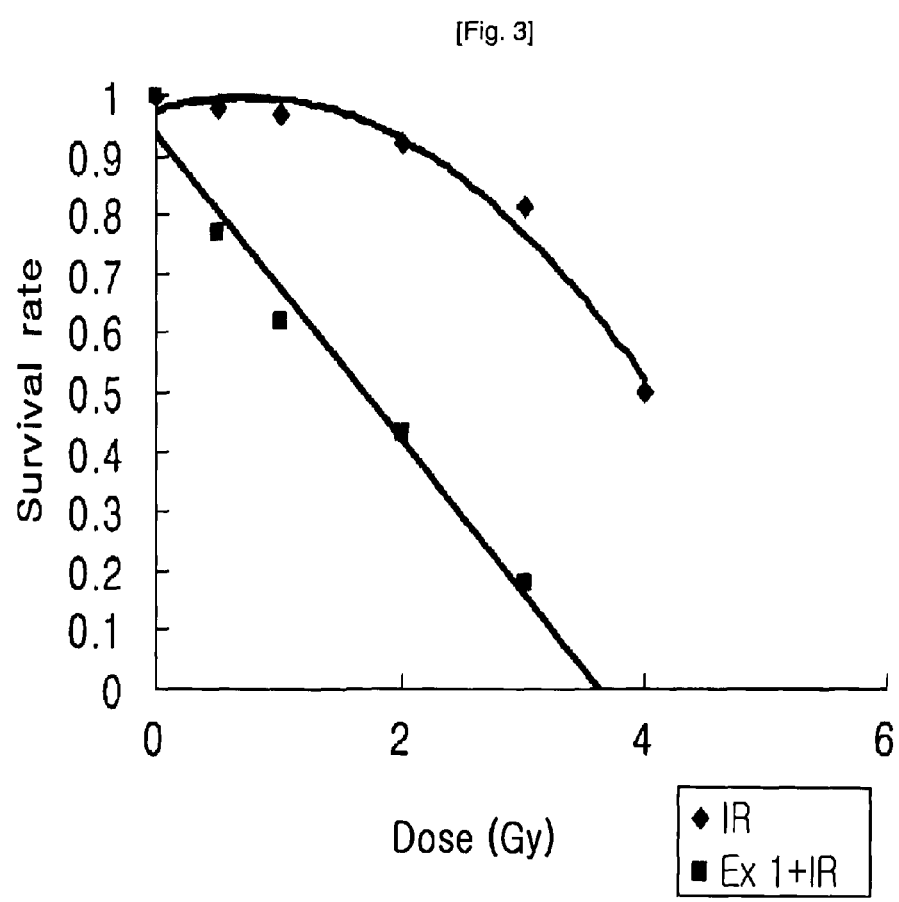

OXAZOLE HYDROXAMIC ACID DERIVATIVES AND USE THEREOF

TECHNICAL FIELD

The present invention relates to an oxazole derivative useful for inhibition of histone deacetylase. More specifically, the present invention relates to an oxazole hydroxamic acid derivative useful for inhibition of histone deacetylase and use thereof.

BACKGROUND ART

Histones are basic proteins which are associated with nuclear DNA of eukaryotic cells and in which reversible acetylation of the lysine residues occurs at certain positions of histone molecules. It is considered that such acetylation of histone proteins is involved in formation of high-order structures of chromatin, which plays a role in regulation of expression of genetic information in conjunction with non-histone proteins.

Regulation of transcription is a critical factor in differentiation, proliferation and death of cells and such cellular processes are controlled by a degree of acetylation of nucleosomal histones. Histone deacetylase (hereinafter, referred to as HDAC) and histone acetyltransferase (hereinafter, referred to as HAT) are related to acetylation of histone which plays a role to regulate gene expression. In particular, among a variety of nuclear processes, regulation of transcription is crucial for regulation of a cell cycle, and occurrence of disorders or dysfunctions in cell cycle regulation may result in diseases such as cancers and inflammation.

There has recently been found the fact that an HDAC inhibitor inhibits growth of various types of cancer cells or induces apoptosis thereof (Bandyopadhyay D et al. (2004) Cancer Research, 64, 7706-7710). Numerous HDAC inhibitors are currently undergoing clinical testing on patients, for treatment purpose of blood cancers and solid cancers. In addition, it was also reported that the HDAC inhibitor is involved in cell proliferation and differentiation, and therefore exhibits anti-autoimmune properties against autoimmune diseases such as arthritis, lupus, and the like diseases, and has neuroprotective and anti-inflammatory effects (Spira et al. (2003) Current Opinion in Pharmacology, 3, 338-343, Marks et al. (2001) Nature review cancer, 1, 194-202). Further, the recently published article has reported the possibility that the HDAC inhibitor may exert therapeutic effects on obesity or diabetes (Picard et al. (2004), Nature, 429, 771-776). Additionally, the HDAC inhibitor, due to anti-cancer effects thereof, may be utilized as a sensitizing agent in chemotherapy or radiotherapy. Recently, it is known that the HDAC inhibitor may be used in treatments via virus-induction such as in HIV (Cohen J et al. (2005), Science, 12, 999-1000).

DISCLOSURE OF INVENTION

Technical Problem

As a result of extensive and intensive research and study, the inventors of the present invention have synthesized an oxazole hydroxamic acid derivative and a pharmaceutically useful salt thereof, which are capable of inhibiting activity of histone deacetylase, and have found that the oxazole derivative thus prepared has anti-cancer activity as well as therapeutic and prophylactic effects on a variety of diseases. Therefore, the present invention has been completed based on these findings.

Therefore, it is an object of the present invention to provide an oxazole hydroxamic acid derivative capable of inhibiting activity of histone deacetylase, and a pharmaceutically useful salt thereof.

Another object of the present invention is to provide a method for preparing an oxazole hydroxamic acid derivative useful as a histone deacetylase inhibitor, and a pharmaceutically useful salt thereof.

Another object of the present invention is to provide a pharmaceutical composition comprising an oxazole hydroxamic acid derivative capable of inhibiting activity of histone deacetylase as an active ingredient and a pharmaceutically acceptable carrier.

Another object of the present invention is to provide use of an oxazole hydroxamic acid derivative as a histone deacetylase inhibitor comprising the same as an active ingredient.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a photograph showing Western blot patterns of histone H3 and H4 antibodies in Experimental Example 3;

FIG. 2 is a bar graph showing improved apoptotic effects on cancer cells upon combined treatment of an oxazole hydroxamic acid derivative in accordance with the present invention with radiation in Experimental Example 6; and FIG. 3 is a graph showing improved inhibition on colony-forming ability of cancer cells upon combined treatment of an oxazole hydroxamic acid derivative in accordance with the present invention with radiation in Experimental Example 6.

BEST MODE FOR CARRYING OUT THE INVENTION

In accordance with an aspect of the present invention, the above and other objects can be accomplished by the provision of an oxazole hydroxamic acid derivative represented by Formula 1:

(Formula 1)

wherein, $R_1$ is alkyl (-SAC (saturated carbon)), or represents alkyl, cycloalkyl (-SCAC), aryl (—Ar), in which allyl-containing double bonds are substituted, or aryl-substituted alkyl (-SAC—Ar), preferably aryl (—Ar);

$R_2$ is alkyl (-SAC), or represents alkyl, cycloalkyl (-SCAC), aryl (—Ar), in which allyl-containing double bonds are substituted, or aryl-substituted alkyl (-SAC—Ar), preferably aryl (—Ar);

n is an integer ranging from 4 to 8; and

X is hydroxy, amino, alkyl (-SAC), or represents alkyl, cycloalkyl (-SCAC), aryl (—Ar), in which allyl-containing double bonds are substituted, or aryl-substituted alkyl (-SAC—Ar), preferably hydroxy; and a pharmaceutically useful salt thereof.

In accordance with another aspect of the present invention, there is provided a method for preparing an oxazole hydroxamic acid derivative and a pharmaceutically useful salt thereof.

In accordance with a further aspect of the present invention, there is provided a pharmaceutical composition comprising an oxazole hydroxamic acid derivative as an active ingredient and a pharmaceutically acceptable carrier.

In accordance with yet another aspect of the present invention, there is provided a use of an oxazole hydroxamic acid derivative as a histone deacetylase inhibitor comprising an oxazole hydroxamic acid derivative or a pharmaceutically useful salt thereof as an active ingredient.

Hereinafter, the present invention will be described in more detail.

HDAC plays a key role in a transcription mechanism regulating gene expression via catalyzation of acetylation of histone which is important for gene expression. Therefore, the term "HDAC inhibitor" as used herein means that the HDAC inhibitor can be used for the treatment and prevention of diseases which results from abnormal gene expression. Examples of diseases that can be effectively treated or prevented by the HDAC inhibitor include various cancers such as blood cancers and solid cancers, inflammation, diabetes, homozygous thalassemia, cirrhosis, acute promyelocytic leukemia (APL), fibrosis, organ transplant rejection, autoimmune diseases, infectious diseases, central nervous system (CNS) diseases such as senile dementia, Huntington's disease (HD) and schizophrenia, cardiovascular diseases such as cardiac hypertrophy and cardiovascular restenosis, osteoporosis (Vega R et al. (2004), Cell, 119, 555-566), conditions and symptoms related to influenza or various viral infections, lower abdominal pain and neck pain, headache, odontalgia, sprain and myositis, arthritis including rheumatic arthritis, degenerative articular diseases, gout and ankylosing spondylitis, tendonitis and psoriasis.

In accordance with the present invention, provided are the oxazole hydroxamic acid derivative and pharmaceutically useful salt thereof, which are useful as the histone deacetylase inhibitor that is effective for the treatment and prevention of the above-illustrated diseases, particularly cancers or inflammation. The oxazole hydroxamic acid derivative and pharmaceutically useful salt thereof in accordance with the present invention are represented by the following Formula 1:

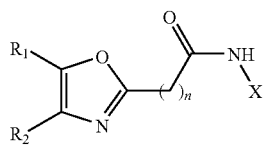

(Formula 1)

wherein, $R_1$ is alkyl (-SAC), or represents alkyl, cycloalkyl (-SCAC), aryl (—Ar), in which allyl-containing double bonds are substituted, or aryl-substituted alkyl (-SAC—Ar), preferably aryl (—Ar);

$R_2$ is alkyl (-SAC), or represents alkyl, cycloalkyl (-SCAC), aryl (—Ar), in which allyl-containing double bonds are substituted, or aryl-substituted alkyl (-SAC—Ar), preferably aryl (—Ar);

n is an integer ranging from 4 to 8; and

X is hydroxy, amino, alkyl (-SAC), or represents alkyl, cycloalkyl (-SCAC), aryl (—Ar), in which allyl-containing double bonds are substituted, or aryl-substituted alkyl (-SAC—Ar), preferably hydroxyl.

In substituents $R_1$ and $R_2$ of the compound 1 in accordance with the present invention, alkyl, cycloalkyl and aryl can be more specifically defined as follows.

As used herein, the term "alkyl" refers to a saturated or unsaturated, linear or branched hydrocarbon group, that contains 1 to 10 carbon atoms. Here, one or more hydrogen atoms in the alkyl group may be substituted with at least one substituent selected from the group consisting of acyl, amino, carboalkoxy, carboxy, carboxyamino, cyano, halo, hydroxy, nitro, thio, alkyl, cycloalkyl, alkoxy, aryloxy, sulfoxy and guanido, wherein hydrogen atoms may be substituted to the substitutable maximum numbers regardless of sequences and kinds of those substituents.

As used herein, the term "cycloalkyl" refers to 3 to 12-membered alkyl having a ring structure, that includes saturated or partially unsaturated hydrocarbon and that may contain 0 to 5 hetero atoms such as oxygen, sulfur and nitrogen, wherein the ring is a 3 to 12-membered single ring or fused ring compound. Here, one or more hydrogen atoms in the cycloalkyl group may be substituted with at least one substituent selected from the group consisting of acyl, amino, carboalkoxy, carboxy, carboxyamino, cyano, halo, hydroxy, nitro, thio, alkyl, cycloalkyl, alkoxy, aryloxy, sulfoxy and guanido, wherein hydrogen atoms may be substituted to the substitutable maximum numbers regardless of sequences (order) and kinds of those substituents.

Specific examples of the cycloalkyl group may include cyclopropyl, cyclobutyl, cyclopentyl, cyclohexyl, cycloheptyl, cyclooctyl, morpholinyl, homomorpholinyl, thiomorpholinyl, homothiomorpholinyl, thiomorpholinyl S-oxide, thiomorpholinyl S,S-ioxide, piperidinyl, homopiperidinyl, piperazinyl, homopiperazinyl, pyrrolidinyl, pyrrolinyl, tetrahydropyranyl, tetrahydrofuranyl, tetrahydrothienyl, oxazolidinonyl, dihydropyrazolyl, dihydropyrrolyl, dihydropyrazinyl, dihydropyridinyl, dihydropyrimidinyl, dihydrofuryl, dihydropyranyl and the like.

As used herein, the term "aryl" is intended to include both aromatic groups consisting of 5 to 15-membered unsaturated hydrocarbons having a single or fused ring structure and hetero aromatic groups that contain 1 to 5 hetero atoms such as oxygen, sulfur and nitrogen. Here, one or more hydrogen atoms in the aryl group may be substituted with at least one substituent selected from the group consisting of acyl, amino, carboalkoxy, carboxy, carboxyamino, cyano, halo, hydroxy, nitro, thio, alkyl, cycloalkyl, alkoxy, aryloxy, sulfoxy and guanido, wherein hydrogen atoms may be substituted to the substitutable maximum numbers regardless of sequences and kinds of those substituents.

Specific examples of the aryl group may include phenyl, 1-naphthyl, 2-naphthyl, pyridinyl, pyrimidinyl, quinolinyl, benzothienyl, indolyl, pyrazinyl, isoindolyl, isoquinolyl, quinazolinyl, quinoxalinyl, phthalazinyl, imidazolinyl, isoxazolyl, pyrazolyl, oxazolyl, thiazolyl, indolizinyl, indazolyl, benzothiazolyl, benzimidazolyl, benzofuranyl, thienyl, pyrrolyl, oxadiazolyl, thiadiazolyl, triazolyl, tetrazolyl, oxazolopyridinyl, imidazopyridinyl, isothiazolyl, cinnolinyl, carbazolyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiopyranyl, benzopyranyl, benzothiopyranyl, coumarinyl, isocoumarinyl, chromonyl, chromanonyl, pyridinyl-N-oxide, tetrahydroquinolinyl-N-oxide, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl-N-oxide, pyrimidinyl-N-oxide, pyrazinyl-N-oxide, quinolinyl-N-oxide, indolyl-N-oxide, indolinyl-N-oxide, pyrazinyl-N-oxide, isoquinolyl-N-oxide, qunazolinyl-N-oxide, quinoxalinyl-N-oxide, phthalazinyl-N-oxide, imidazolinyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-N-oxide, oxadiazolyl-N-oxide, thiadiazolyl-N-oxide, triazolyl-N-oxide, tetrazolyl-N-oxide and the like.

As used herein, the term "halo" names generically fluoro, chloro, bromo and iodo.

Meanwhile, for convenience of explanation, abbreviated designations are used for the following compounds throughout the present specification:

N,N-dimethyl formamide: DMF
Tetrahydrofuran: THF
Triethylamine: TEA
Methyl: Me
Ethyl: Et Among oxazole hydroxamic acid derivatives of Formula 1, particularly preferred examples may be the following compounds (1) to (20):

(1) 7-(5-(4-methoxy-phenyl)-4-phenyl-oxazol-2-yl)-heptanoic acid hydroxyamide
(2) 7-[5-(2-methoxy-phenyl)-4-phenyl-oxazol-2-yl-heptanoic acid hydroxyamide
(3) 7-[5-(3-methoxy-phenyl)-4-phenyl-oxazol-2-yl-heptanoic acid hydroxyamide
(4) 7-(4,5-diphenyl-oxazol-2-yl)-heptanoic acid hydroxyamide
(5) 7-[5-(2-fluoro-phenyl)-4-phenyl-oxazol-2-yl]-heptanoic acid hydroxyamide
(6) 7-[5-(3-fluoro-phenyl)-4-phenyl-oxazol-2-yl]-heptanoic acid hydroxyamide
(7) 7-(4-phenyl-5-p-tolyl-oxazol-2-yl)-heptanoic acid hydroxyamide
(8) 7-[5-(4-ethoxy-phenyl)-4-phenyl-oxazol-2-yl]-heptanoic acid hydroxyamide
(9) 7-[5-(4-fluoro-phenyl)-4-phenyl-oxazol-2-yl]-heptanoic acid hydroxyamide
(10) 7-[4,5-bis-(4-methoxy-phenyl)oxazol-2-yl]-heptanoic acid hydroxyamide
(11) 7-[4-(2-methoxy-phenyl)-5-(4-methoxy-phenyl)-oxazol-2-yl]-heptanoic acid hydroxyamide
(12) 7-[5-(4-dimethylamino-phenyl)-4-phenyl-oxazol-2-yl]-heptanoic acid hydroxyamide
(13) 7-[4-(4-methoxy-phenyl)-5-pyridin-3-yl-oxazol-2-yl]-heptanoic acid hydroxyamide
(14) 7-[4-(4-dimethylamnino-phenyl)-5-pyridin-3-yl-oxazol-2-yl]-heptanoic acid hydroxyamide
(15) 7-[4-(4-fluoro-phenyl)-5-pyridin-3-yl-oxazol-2-yl]-heptanoic acid hydroxyamide
(16) 7-[4-(3-fluoro-phenyl)-5-pyridin-3-yl-oxazol-2-yl]-heptanoic acid hydroxyamide
(17) 7-(4-phenyl-5-pyridin-4-yl-oxazol-2-yl)-heptanoic acid hydroxyamide
(18) 7-[5-(4-methoxy-phenyl)-4-pyridin-4-yl-oxazol-2-yl)-heptanoic acid hydroxyamide
(19) 7-[5-(4-ethoxy-phenyl)-4-pyridin-4-yl-oxazol-2-yl)-heptanoic acid hydroxyamide
(20) 7-[5-(4-hydroxy-phenyl)-4-phenyl-oxazol-2-yl]-heptanoic acid hydroxyamide Further, the present invention also provides a method for preparing the oxazole hydroxamic acid derivative of Formula 1 and a pharmaceutically useful salt thereof.

A person having ordinary skill for synthesis of compounds in the art to which the present invention pertains will appreciate that it will be possible to prepare the oxazole hydroxamic acid derivative of Formula 1 in accordance with the present invention, using known compounds, or compounds that can be easily prepared from such known compounds. Therefore, the following description regarding preparation of the oxazole hydroxamic acid derivative of Formula 1 in accordance with the present invention presents only illustrative examples of preparation methods thereof, which may involve changes and modifications in sequences of unit operations, steps or the like, and it should be understood that the scope of the present invention is not limited thereto.

Depending upon starting materials, the oxazole hydroxamic acid derivative of Formula I in accordance with the present invention may be prepared with reference to any one of the following reaction schemes 1 to 5.

Hereinafter, the method for preparing the oxazole hydroxamic acid derivative according to the reaction scheme 1 will be specifically described on the basis of respective steps.

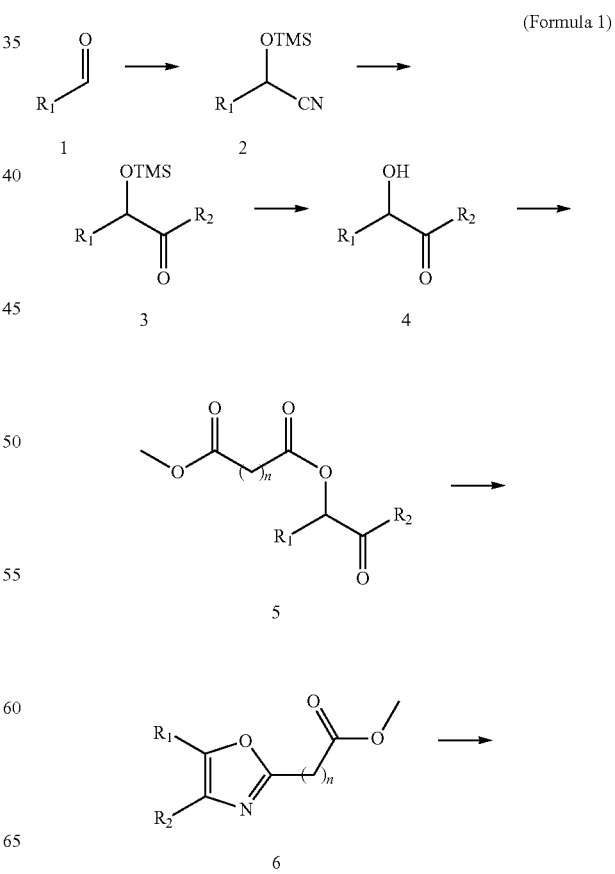

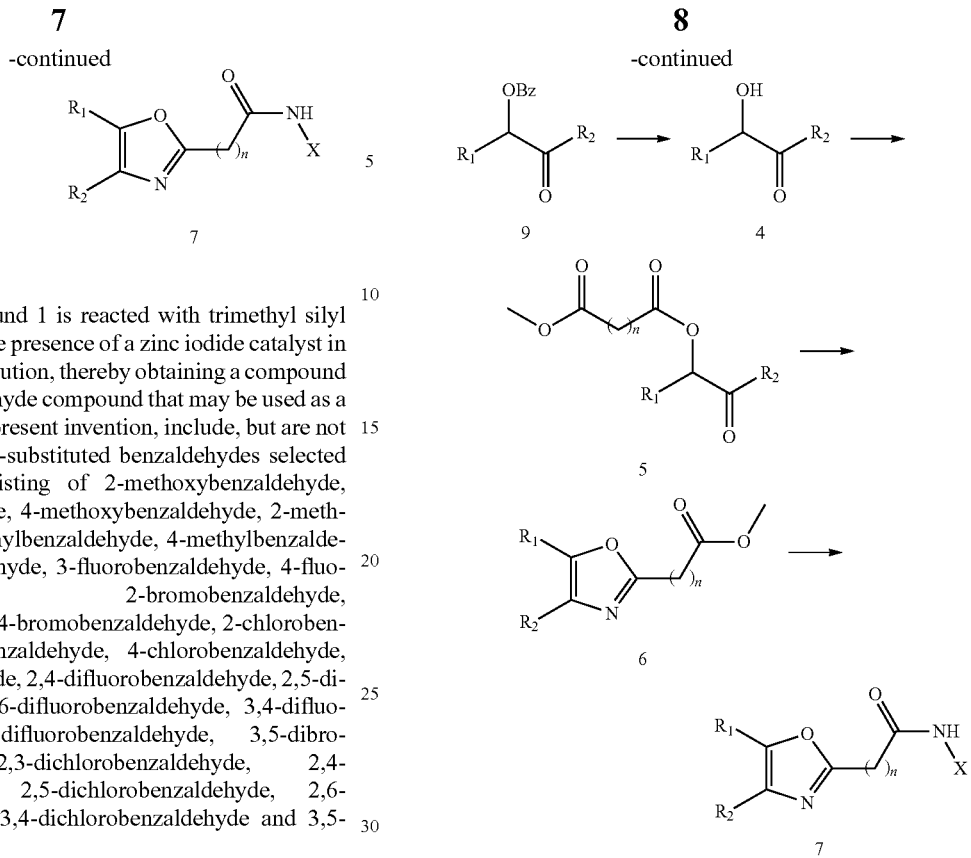

An aldehyde compound 1 is reacted with trimethyl silyl cyanide (TMSCN) in the presence of a zinc iodide catalyst in a methylene chloride solution, thereby obtaining a compound 2. Examples of the aldehyde compound that may be used as a starting material in the present invention, include, but are not limited to, mono- or di-substituted benzaldehydes selected from the group consisting of 2-methoxybenzaldehyde, 3-methoxybenzaldehyde, 4-methoxybenzaldehyde, 2-methylbenzaldehyde, 3-methylbenzaldehyde, 4-methylbenzaldehyde, 2-fluorobenzaldehyde, 3-fluorobenzaldehyde, 4-fluorobenzaldehyde, 2-bromobenzaldehyde, 3-bromobenzaldehyde, 4-bromobenzaldehyde, 2-chlorobenzaldehyde, 3-chlorobenzaldehyde, 4-chlorobenzaldehyde, 2,3-difluorobenzaldehyde, 2,4-difluorobenzaldehyde, 2,5-difluorobenzaldehyde, 2,6-difluorobenzaldehyde, 3,4-difluorobenzaldehyde, 3,5-difluorobenzaldehyde, 3,5-dibromobenzaldehyde, 2,3-dichlorobenzaldehyde, 2,4-dichlorobenzaldehyde, 2,5-dichlorobenzaldehyde, 2,6-dichlorobenzaldehyde, 3,4-dichlorobenzaldehyde and 3,5-dichlorobenzaldehyde.

The compound 2 thus obtained is reacted with $R_2MgBr$ wherein $R_2$ is aryl, most preferably phenyl, thereby preparing a compound 3. An aqueous 90% trifluoro acetic acid solution is added to the compound 3 to prepare a compound 4 from which an O-protective group was removed, and the compound 4 is reacted with methoxycarbonyl acylchloride having a methylene chain with a varying length in the presence of an amine base such as triethylamine, thereby obtaining compound 5. Here, examples of the acylchloride compound used for introduction of the methylene chains (n) having a varying length may include, but are not limited to, those selected from the group consisting of 3-(carbomethoxy)propionyl chloride, methyl 4-(chloroformyl)butyrate, methyl 5-(chloroformyl)pentanoate, 6-(chloroformyl)hexanoic acid ethyl ester, methyl 8-chloro-8-oxooctanoate, methyl 9-chloro-9-oxononanoate and methyl 10-chloro-10-oxodecanoate.

Then, the compound 5 thus obtained is reacted with ammonium acetate in an acetic acid solution to obtain an oxazole compound 6. The thus-obtained oxazole compound 6 is reacted with a suitable amine such as ammonia, hydrazine or hydroxylamine, thereby obtaining a final compound 7 (compound of Formula 1).

Hereinafter, the method for preparing the oxazole hydroxamic acid derivative according to the reaction scheme 2 will be specifically described on the basis of respective steps.

First, an aldehyde compound 1 is reacted with sodium cyanide and benzoyl chloride in the presence of a benzyltriethylammonium chloride catalyst, thereby preparing a compound 8. The compound 8 is reacted with sodium hydride and aldehyde to obtain a compound 9 which is then added to a 1.0M potassium tert-butoxide solution, thereby obtaining a compound 4 from which an O-protective group was removed. Subsequent processes are carried out in the same manner as in Scheme 1.

Hereinafter, the method for preparing the oxazole hydroxamic acid derivative according to the reaction scheme 3 will be described on the basis of respective steps.

[Scheme 3]

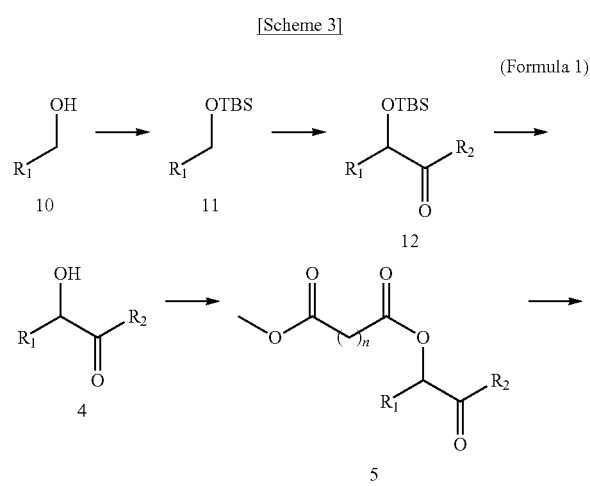

(Formula 1)

[Scheme 2]

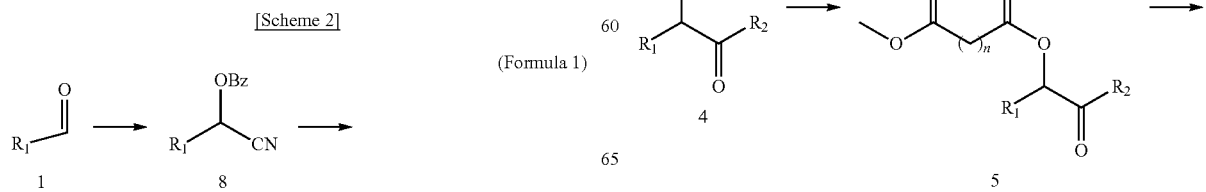

(Formula 1)

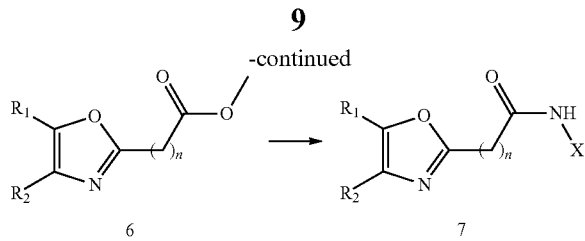

First, a methanol derivative compound 10, for example 4-pyridinecarbinol, as a starting material, is reacted with tetrabutyldimethyl silyl chloride and imidazole to prepare an O-protected compound 11. The compound 11 is reacted with lithium di-amide and N-methoxy-N-methylamide derivative, for example N-methoxy-N-methylbenzamide, to obtain a compound 12. The compound 12 is treated with tetrabutyl ammonium fluoride to obtain an intermediate compound 4. Subsequent processes are the same as in Scheme 1.

Hereinafter, the method for preparing the oxazole hydroxamic acid derivative according to the reaction scheme 4 will be described on the basis of respective steps.

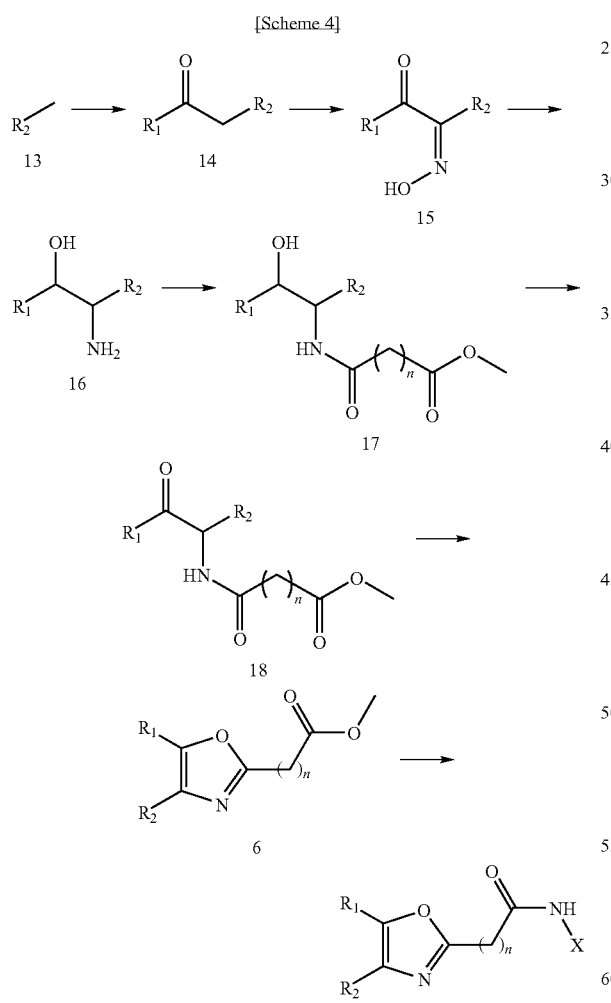

First, a methane derivative compound 13, for example 4-methylpyridine or 4-ethoxy-N-methylbenzamide, as a starting material, is reacted with lithium bistrimethyl silyl amide and substituted N-methoxy-N-methyl amide to thereby prepare a compound 14. The compound 14 is treated with sodium nitrite and acid, for example hydrochloric acid, to obtain an oxime compound 15. The resulting oxime compound 15 is hydrogenated using a palladium catalyst to obtain a compound 16. Next, through the same reaction as in the synthesis process of the compound 5 of reaction scheme 1, a compound 17 can be synthesized in which a methylene chain was introduced into an amine group. The compound 17 is subjected to Swern oxidation, then reacted with triphenyl phosphine, iodine and triethyl amine to obtain an intermediate compound 6. Subsequent processes are the same as in Scheme 1.

Hereinafter, the method for preparing the oxazole hydroxamic acid derivative according to the reaction scheme 5 will be specifically described on the basis of respective steps.

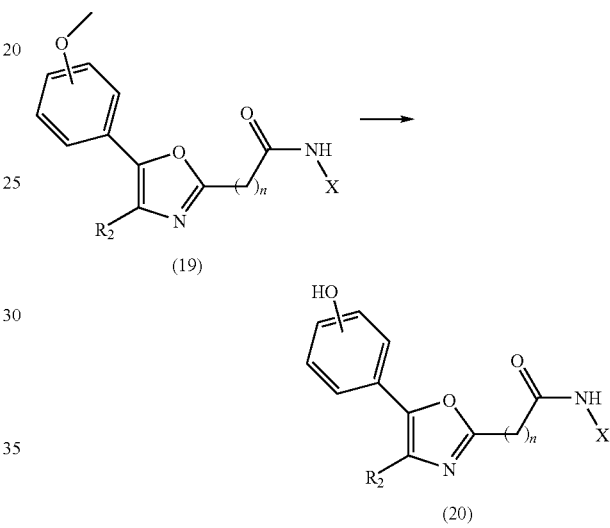

Where $R_1$ of Formula 1 in accordance with the present invention is hydroxyphenyl, a final compound 20 can be obtained using a starting material 19 having a methoxyphenyl group as a substituent, for example 7-(5-4-methoxyphenyl)-4-phenyloxazol-2-yl)heptanoic acid hydroxyamide and a 1.0 M tribromoborane solution.

According to the present invention, there is provided a pharmaceutical composition comprising a therapeutically effective amount of an oxazole hydroxamic acid derivative represented by Formula 1 and a pharmaceutically acceptable carrier.

According to the present invention, it is possible to prepare an oxazole hydroxamic acid derivative useful for inhibition of histone deacetylase and a pharmaceutically useful salt thereof. In addition, it can be seen that the-thus prepared compound, as will be illustrated by clinical testing in the following Experimental Examples, is effective for the treatment and prevention of various diseases, resulting from abnormal gene expression by histone. Examples of diseases that can be treated or prevented by inhibition of histone deacetylase include various cancers such as blood cancers and solid cancers, inflammation, diabetes, homozygous thalassemia, cirrhosis, acute promyelocytic leukemia (APL), fibrosis, organ transplant rejection, autoimmune diseases, infectious diseases, central nervous system (CNS) diseases such as Huntington's disease (HD) and schizophrenia, cardiovascular diseases such as cardiac hypertrophy and cardiovascular restenosis, conditions and symptoms related to influenza or various viral infections, pain, headache, odontalgia, sprain and myositis, arthritis including rheumatic arthritis, degenerative articular diseases, gout and ankylosing spondylitis, tendonitis and psoriasis.

The oxazole hydroxamic acid derivative of Formula 1 in accordance with the present invention may be formulated into various pharmaceutical dosage forms depending on desired purpose. In preparing the pharmaceutical composition in accordance with the present invention, an active ingredient, specifically the oxazole hydroxamic acid derivative of Formula 1 is mixed with a variety of pharmaceutically acceptable carriers that can be selected depending on desired formulation to be prepared.

The active ingredient may be, depending on desired purpose, formulated into injectable preparations, transdermal preparations or oral preparations and for easy administration and uniform dose, it is preferably prepared in a unit dosage form.

In preparing formulations intended for oral administration, a conventional pharmaceutically acceptable carrier may be used. For example, in the case of liquid oral preparations such as suspensions, syrups, elixirs and solutions, water, glycol, oil and alcohol may be used as the carrier. For solid forms of preparations such as powders, pills, capsules and tablets, starch, sucrose, kaolin, lubricant, binder and disintegrant may be used as the carrier. For easy administration, the most convenient dosage forms are tablets and capsules, and tablets and pills are preferably prepared in enteric coating.

In the case of parenteral preparations, sterilized water is conventionally used as the carrier, and other ingredients such as dissolution aids can be included. Injectable preparations, for example aqueous or oily suspensions for sterile injection may be prepared using suitable dispersants, wetting agents or suspending agents by known techniques. Solvents used herein may include water, Ringer's solution and isotonic NaCl solution, and sterile fixed oil is also conventionally used as the solvent or suspending medium. Any non-irritable fixed oil including mono- and di-glyceride may be used for such purpose and further, fatty acids such as oleic acid may be used in the injectable preparation.

In the case of transdermal preparations, penetration promoters and/or suitable wetting agents as the carrier may be used optionally in combination with a suitable additive that is non-irritable to skin. The additive is selected from those that promote administration through skin and assist in preparing a desired composition. Transdermal preparation may be administered in various manners such as transdermal patches, creams or ointments.

In order to prevent active ingredients from being rapidly removed from the body, the composition in accordance with the present invention may be formulated in the form of sustained-release preparations. In this connection, usable carriers include, but are not limited to, implants, microencapsulated delivery systems, and biodegradable/biocompatible polymers, which are known in the art.

The term "therapeutically effective amount" as used herein means an amount of active ingredient effective to alleviate or reduce symptoms of a disease in need of treatment, or to reduce or retard the onset of clinical markers or symptoms of a disease in need of prevention. The therapeutically effective amount may be empirically determined by experimenting with compounds of interest in known in vivo and in vitro model systems for a disease in need of treatment.

When the active ingredient, specifically the oxazole hydroxamic acid derivative of Formula 1 in accordance with the present invention is administered for clinical purpose, a total daily dose that will be administered into a host at a single dose or divided dose is preferably in a range of 0.1 to 100 mg/kg of BW, but a specific dose level for certain patients may be varied depending on kinds of compounds to be used, the body weight, age, sex and conditions of patients, dietary regimen, administration time of drugs, administration routes, excretion rate, mixing of drugs, and severity of disease and the like.

If necessary, the oxazole hydroxamic acid derivative of Formula 1 in accordance with the present invention can be used for formulation of a pharmaceutical composition which is effective in the form of a prodrug thereof.

As discussed above, the oxazole hydroxamic acid derivative represented by Formula 1 encompasses pharmaceutically acceptable salts thereof. Such pharmaceutically acceptable salts are not particularly limited so long as they retain activity of a parent compound within the subject to be administered, and do not cause undesirable effects. Such salts include inorganic and organic salts, and preferably may include, but are not limited to, salts of the following acids: acetic, nitric, aspartic, sulfonic, sulfuric, maleic, glutamic, formic, succinic, phosphoric, phthalic, tannic, tartaric, hydrobromic, propionic, benzenesulfonic, benzoic, stearic, esyl, lactic, bicarbonic, bisulfuric, bitartaric, oxalic, butyric, calcium edetate, camsylic, carbonic, chlorobenzoic, citric, edetic, toluenesulfonic, edisylic, esylic, fumaric, glucceptic, pamoic, gluconic, glycollylarsanilic, methylnitric, polygalactouronic, hexylresorcinoic, malonic, hydrabamic, hydrochloric, hydroiodic, hydroxynaphthoic, isethionic, lactobionic, mandelic, estolic, methylsulfuric, mucic, napsylic, muconic, p-nitromethanesulfonic, hexamic, pantothenic, monohydrogen phosphoric, dihydrogen phosphoric, salicylic, sulfamic, sulfanilic, methanesulfonic and teoclic acids.

The HDAC inhibitor composition in accordance with the present invention may further include other ingredients that do not inhibit action of the active ingredient or assist in action of the active ingredient, and may be formulated into various forms known in the art.

MODE FOR THE INVENTION

Examples

Now, the present invention will be described in more detail with reference to the following Examples. These examples are provided only for illustrating the present invention and should not be construed as limiting the scope and spirit of the present invention.

Example 1

Preparation of 7-(5-(4-methoxyphenyl)-4-phenyloxazol-2-yl)heptanoic acid hydroxyamide The above title compound was prepared according to the following reaction scheme 6:

[Scheme 6]

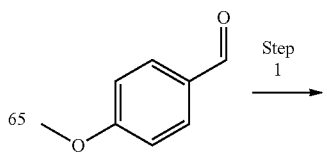

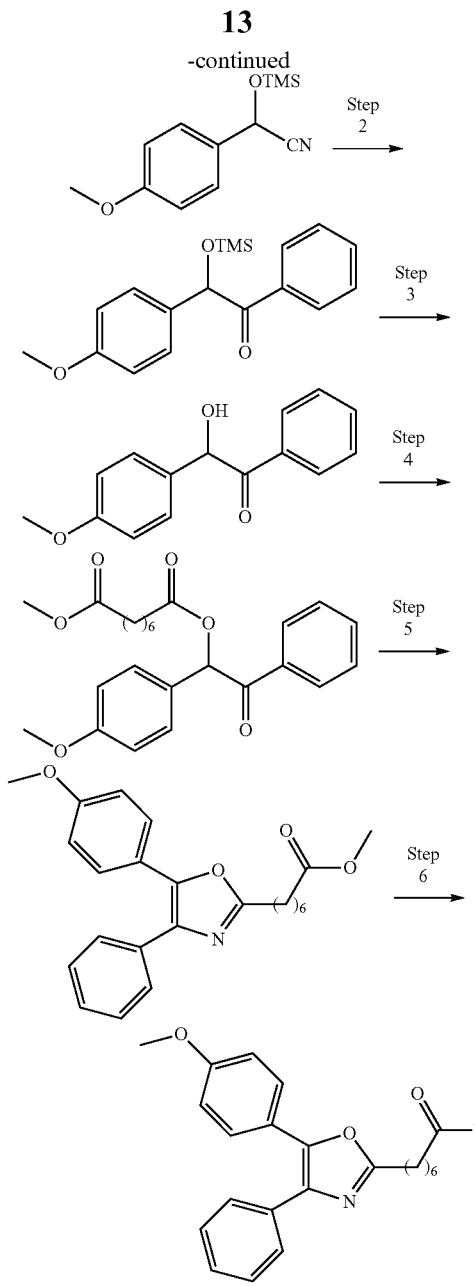

Step 2: Preparation of 2-(4-methoxyphenyl)-1-phenyl-2-trimethylsilanyloxy-ethanone To a diluted solution of 3.0 M phenylmagnesium bromide (Aldrich, 39 mL, 0.12 mol) in anhydrous diethyl ether (500 mL) was slowly added a solution of (4-methoxyphenyl)-trimethylsilanyloxy-acetonitrile (36.13 g, 0.11 mol), which obtained in Step 1, in anhydrous diethyl ether (50 mL) at 4° C. After addition was complete, the reaction solution was elevated to room temperature and stirred for 2 hours. The reaction was quenched by slow addition of 3N HCl solution (200 ml). After separation of an organic layer and aqueous layer, the thus-obtained organic layer was washed twice with 100 mL of a saturated sodium bicarbonate solution and then successively washed twice with 100 mL of a brine solution. The organic layer obtained was dried over magnesium sulfate, filtered and concentrated under reduced pressure, to give 30.54 g (yield: 85%) of 2-(4-methoxyphenyl)-1-phenyl-2-trimethylsilanyloxy-ethanone as a desired product.

$^1$H-NMR (CDCl$_3$, 200 MHz), ppm (d): 0.21 (s, 9H), 3.89 (s, 3H), 5.45 (s, 1H), 6.95 (d, 2H), 7.38 (d, 2H)

Step 3: Preparation of 2-hydroxy-2-(4-methoxyphenyl)-1-phenyl-ethanone 30 g (0.091 mol) of 2-(4-methoxyphenyl)-1-phenyl-2-trimethylsilanyloxy-ethanone prepared in Step 2 was added to 50 mL of an aqueous 90% trifluoroacetic acid solution and the resulting reaction solution was stirred at room temperature for 2 hours. An ice bath was placed and the resulting reaction solution was neutralized with addition of sodium carbonate. Then, 200 mL of ethyl acetate and 100 mL of water were added to dilute the solution, followed by separation of layers. The obtained organic layer was washed twice with 100 mL of a saturated sodium bicarbonate solution and then successively washed twice with 100 mL of a brine solution. The organic layer thus obtained was dried over magnesium sulfate, filtered and concentrated under reduced pressure to give 17.25 g of a final product which was then recrystallized from ethyl acetate and hexane, to give 14.38 g (yield: 65%) of pure 2-hydroxy-2-(4-methoxyphenyl)-1-phenyl-ethanone.

$^1$H-NMR (CDCl$_3$, 200 MHz), ppm (d): 4.04 (s, 3H), 6.18 (s, 1H), 7.09 (d, 2H), 7.48 (d, 2H), 7.61-8.13 (m, 5H)

Step 4: Preparation of octanedioic acid 1-(4-methoxyphenyl)-2-oxo-2-phenylethyl ester methyl ester To a solution of 2-hydroxy-2-(4-methoxyphenyl)-1-phenyl-ethanone (8.2 g, 0.034 mol) prepared in Step 3 and triethylamine (5.21 g, 0.051 mol) in methylene chloride (100 mL) was slowly added a solution of 7-chlorocarbonylheptanoic acid methyl ester (5.64 g, 0.034 mol) in methylene chloride (20 mL). A final reaction solution was stirred at room temperature for 12 hours and then diluted with 200 mL of methylene chloride. The obtained organic layer was washed twice with 100 mL of a saturated sodium bicarbonate solution and then successively washed twice with 100 mL of a brine solution. The obtained organic layer was dried over magnesium sulfate, filtered and concentrated under reduced pressure, to give 12.90 g (yield: 92%) of octanedioic acid 1-(4-methoxyphenyl)-2-oxo-2-phenylethyl ester methyl ester.

$^1$H-NMR (CDCl$_3$, 200 MHz), ppm (d): 1.34 (m, 4H), 1.65 (m, 4H), 2.26 (m, 2H), 2.43 (m, 2H), 3.65 (s, 3H), 3.77 (s, 3H), 5.91 (s, 1H), 6.89-7.93 (m, 9H)

Step 1: Preparation of (4-methoxyphenyl)-trimethylsilanyloxy-acetonitrile

To a solution of 4-methoxybenzaldehyde (38.94 g, 0.286 mol) and zinc iodide (0.92 g, 2.86 mmol) in methylene chloride (200 mL) was slowly added a solution of trimethylsilyl cyanide (29.2 g, 0.294 mol) in methylene chloride (50 mL). The reaction solution was stirred at room temperature for 2 hours, and then was diluted with additional methylene chloride (400 mL). After the reaction was complete, an organic layer was washed twice with 100 mL of a saturated sodium bicarbonate solution and then successively washed twice with 100 mL of a brine solution. The organic layer thus obtained was dried over magnesium sulfate, filtered and concentrated under reduced pressure, to give 69.65 g (yield: 95%) of a desired product (4-methoxyphenyl)-trimethylsilanyloxy-acetonitrile as brownish oil.

Step 5: Preparation of 7-[5-(4-methoxyphenyl)-4-phenyl-oxazol-2-yl-heptanoic acid methyl ester 10 g (24.24 mmol) of octanedioic acid 1-(4-methoxyphenyl)-2-oxo-2-phenylethyl ester methyl ester according to Step 4 was diluted with addition of 60 mL of acetic acid, followed by addition of 7.56 g (96.96 mmol) of ammonium acetate, and the resulting mixture was heated at 100° C. for 4 hours. After removing an excess added acetic acid under reduced pressure, the concentrated product was diluted with 400 mL of ethyl acetate and 200 mL of water was added to dissolve salts, followed by separation of layers. The obtained organic layer was washed twice with 200 mL of a saturated sodium bicarbonate solution and then successively washed twice with 200 mL of a brine solution. The organic layer was dried over magnesium sulfate, filtered, concentrated under reduced pressure and purified by silica gel column chromatography (developing solvent (mobile phase): mixture of ethyl acetate:hexane in a ratio of 1:9), to give 4.76 g (yield: 50%) of 7-[5-(4-methoxyphenyl)-4-phenyl-oxazol-2-yl-heptanoic acid methyl ester.

$^1$H-NMR (CDCl$_3$, 200 MHz), ppm (d): 1.42 (m, 4H), 1.66 (m, 4H), 2.34 (m, 2H), 2.83 (m, 2H), 3.66 (s, 3H), 3.83 (s, 3H), 6.89-7.93 (m, 9H)

Step 6: Preparation of 7-[5-(4-methoxyphenyl)-4-phenyl-oxazol-2-yl]-heptanoic acid hydroxyamide 4.76 g (12.1 mmol) of 7-[5-(4-methoxyphenyl)-4-phenyl-oxazol-2-yl-heptanoic acid methyl ester prepared in Step 5 was dissolved in 20 mL of a solution of tetrahydrofuran and methanol in a ratio of 1:1, and 3 g of an aqueous 50% N-hydroxylamine solution was added thereto. The reaction solution was stirred at room temperature for 24 hours and then 8 g of an aqueous 50% N-hydroxylamine solution was additionally added thereto, followed by further stirring at room temperature for 48 hours. After removing the solvent under reduced pressure, 100 mL of ethyl acetate and 100 mL of water were added to the resulting solution which was then briefly stirred. The resulting solid materials were filtered and washed with water and diethyl ether, to give 0.19 g of a title compound.

$^1$H-NMR (CD$_3$OD, 200 MHz), ppm (d): 1.42 (m, 4H), 1.66 (m, 4H), 2.34 (m, 2H), 2.83 (m, 2H), 3.83 (s, 3H), 6.95 (m, 2H), 7.38 (m, 2H), 7.85-8.25 (m, 4H)

Compounds of the following Examples 2 through 12 were prepared according to the method of Example 1.

Example 2

Preparation of 7-[5-(2-methoxy-phenyl)-4-phenyl-oxazol-2-yl]-heptanoic acid hydroxyamide 7-[5-(2-methoxy-phenyl)-4-phenyl-oxazol-2-yl]-heptanoic acid hydroxyamide of the following formula was prepared in the same manner as in Example 1, except for 2-methoxybenzaldehyde was used as a starting material.

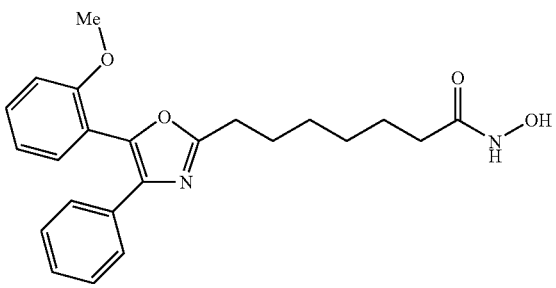

$^1$H-NMR (CDCl$_3$, 200 MHz), ppm (d): 1.19-1.53 (m, 4H), 1.57-1.73 (m, 2H), 1.75-1.93 (m, 2H), 2.03-2.21 (m, 2H), 2.80-2.90 (m, 2H), 3.60 (s, 3H), 6.91-7.13 (m, 2H), 7.20-7.62 (m, 7H), 9.52 (br s, 1H)

Example 3

Preparation of 7-[5-(3-methoxy-phenyl)-4-phenyl-oxazol-2-yl]-heptanoic acid hydroxyamide 7-[5-(3-methoxy-phenyl)-4-phenyl-oxazol-2-yl]-heptanoic acid hydroxyamide of the following formula was prepared in the same manner as in Example 1, except for 3-methoxybenzaldehyde was used as a starting material.

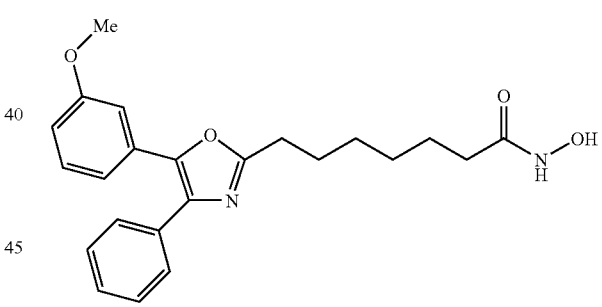

$^1$H-NMR (acetone-d$_6$, 200 MHz), ppm (d): 1.30-1.54 (m, 4H), 1.56-1.74 (m, 2H), 1.75-1.90 (m, 2H), 2.15 (t, 2H), 2.84 (t, 2H), 3.75 (s, 3H), 6.92-7.71 (m, 9H), 9.03 (br s, 1H), 10.13 (br s, 1H)

Example 4

Preparation of 7-(4,5-diphenyl-oxazol-2-yl)-heptanoic acid hydroxyamide 7-(4,5-diphenyl-oxazol-2-yl)-heptanoic acid hydroxyamide of the following formula was prepared in the same manner as in Example 1, except for benzaldehyde was used as a starting material.

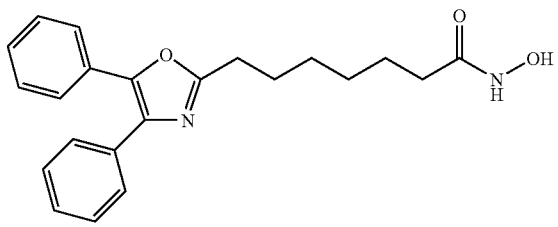

¹H-NMR (acetone-d₆, 200 MHz), ppm (d): 1.28-1.56 (m, 4H), 1.58-1.74 (m, 2H), 1.76-1.96 (m, 2H), 2.15 (t, 2H), 2.84 (t, 2H), 7.30-7.69 (m, 9H), 9.01 (br s, 1H), 10.19 (br s, 1H)

Example 5

Preparation of 7-[5-(2-fluoro-phenyl)-4-phenyl-oxazol-2-yl]-heptanoic acid hydroxyamide 7-[5-(2-fluoro-phenyl)-4-phenyl-oxazol-2-yl]-heptanoic acid hydroxyamide of the following formula was prepared in the same manner as in Example 1, except for 2-fluorobenzaldehyde was used as a starting material.

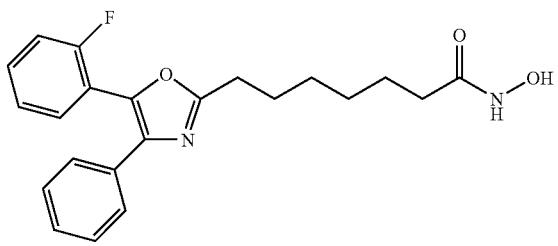

¹H-NMR (acetone-d₆, 200 MHz), ppm (d): 1.24-1.53 (m, 4H), 1.55-1.74 (m, 2H), 1.76-1.97 (m, 2H), 2.01-2.12 (m, 2H), 2.87 (t, 2H), 7.27-7.65 (m, 9H), 8.79 (br s, 1H), 10.06 (br s, 1H)

Example 6

Preparation of 7-[5-(3-fluoro-phenyl)-4-phenyl-oxazol-2-yl]-heptanoic acid hydroxyamide 7-[5-(3-fluoro-phenyl)-4-phenyl-oxazol-2-yl]-heptanoic acid hydroxyamide of the following formula was prepared in the same manner as in Example 1, except for 3-fluorobenzaldehyde was used as a starting material.

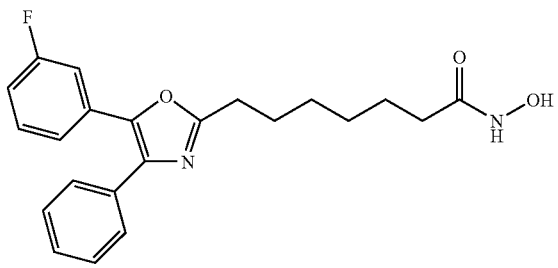

¹H-NMR (acetone-d₆, 200 MHz), ppm (d): 1.28-1.57 (m, 4H), 1.59-1.76 (m, 2H), 1.79-1.96 (m, 2H), 1.99-2.12 (m, 2H), 2.88 (t, 2H), 7.09-7.76 (m, 9H), 10.01 (br s, 1H)

Example 7

Preparation of 7-(4-phenyl-5-p-tolyl-oxazol-2-yl)-heptanoic acid hydroxyamide 7-(4-phenyl-5-p-tolyl-oxazol-2-yl)-heptanoic acid hydroxyamide of the following formula was prepared in the same manner as in Example 1, except for 4-methylbenzaldehyde was used as a starting material.

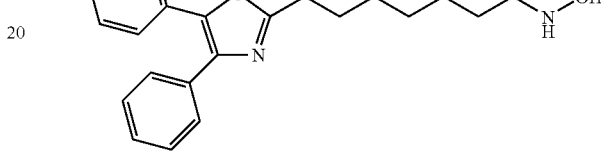

¹H-NMR (CDCl₃, 200 MHz), ppm (d): 1.21-1.58 (m, 4H), 1.59-1.79 (m, 2H), 1.79-1.99 (m, 2H), 2.01-2.21 (m, 2H), 2.38 (s, 3H), 2.84 (t, 2H), 7.15-7.65 (m, 9H), 10.07 (br s, 1H)

Exmple 8

Preparation of 7-[5-(4-ethoxy-phenyl)-4-phenyl-oxazol-2-yl]-heptanoic acid hydroxyamide 7-[5-(4-ethoxy-phenyl)-4-phenyl-oxazol-2-yl]-heptanoic acid hydroxyamide of the following formula was prepared in the same manner as in Example 1, except for 4-ethoxybenzaldehyde was used as a starting material.

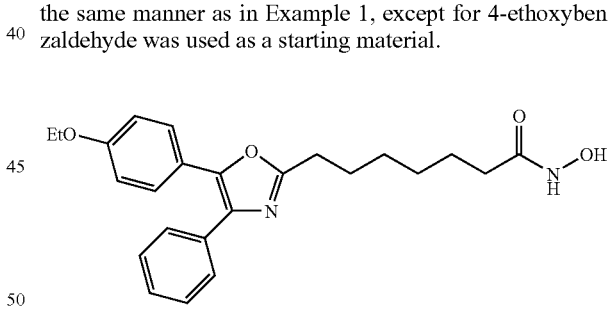

¹H-NMR (CDC₃, 200 MHz), ppm (d): 1.22-1.58 (m, 7H), 1.59-1.79 (m, 2H), 1.79-1.99 (m, 2H), 2.01-2.21 (m, 2H), 2.83 (t, 2H), 4.07 (t, 2H), 6.87 (d, 2H), 7.29-7.64 (m, 7H), 9.98 (br s, 1H)

Example 9

Preparation of 7-[5-(4-fluoro-phenyl)-4-phenyl-oxazol-2-yl]-heptanoic acid hydroxyamide 7-[5-(4-fluoro-phenyl)-4-phenyl-oxazol-2-yl]-heptanoic acid hydroxyamide of the following formula was prepared in the same manner as in Example 1, except for 4-fluorobenzaldehyde was used as a starting material.

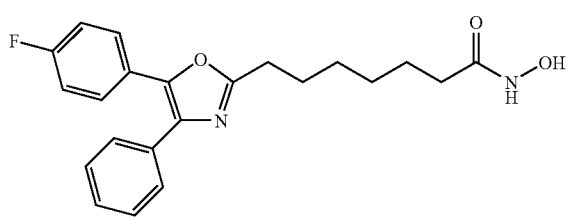

¹H-NMR (CDCl₃, 200 MHz), ppm (d): 1.21-1.48 (m, 4H), 1.49-1.76 (m, 2H), 1.77-1.99 (m, 2H), 2.01-2.21 (m, 2H), 2.83 (t, 2H), 6.99-7.08 (m, 2H), 7.29-7.61 (m, 7H), 10.19 (br s, 1H)

Example 10

Preparation of 7-[4,5-bis-(4-methoxy-phenyl)-oxazol-2-yl]-heptanoic acid hydroxyamide 7-[4,5-bis-(4-methoxy-phenyl)-oxazol-2-yl]-heptanoic acid hydroxyamide of the following formula was prepared in the same manner as in Example 1, except for 4-methoxybenzaldehyde was used as a starting material, and 4-methoxyphenylmagnesium bromide was used in Step 2.

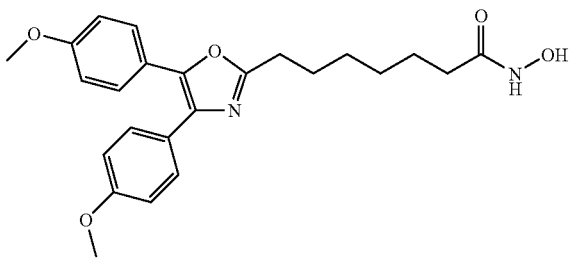

¹H-NMR (CDCl₃, 200 MHz), ppm (d): 1.21-1.51 (m, 4H), 1.51-1.98 (m, 4H), 1.98-2.19 (m, 2H), 2.83 (t, 2H), 3.83 (s, 6H), 6.87-6.93 (m, 4H), 7.47-7.56 (m, 4H)

Example 11

Preparation of 7-[4-(2-methoxy-phenyl)-5-(4-methoxy-phenyl)-oxazol-2-yl]-heptanoic acid hydroxyamide 7-[4-(2-methoxy-phenyl)-5-(4-methoxy-phenyl)-oxazol-2-yl]-heptanoic acid hydroxyamide of the following formula was prepared in the same manner as in Example 1, except for 4-methoxybenzaldehyde was used as a starting material, and 2-methoxyphenylmagnesium bromide was used in Step 2.

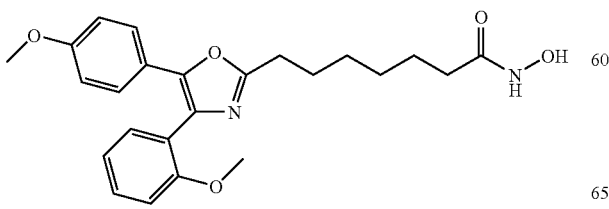

¹H-NMR (CDCl₃, 200 MHz), ppm (d): 1.24-1.46 (m, 4H), 1.48-1.98 (m, 4H), 1.98-2.19 (m, 2H), 2.79-2.99 (m, 2H), 3.65 (s, 3H), 3.81 (s, 3H), 6.84 (d, 2H), 6.86-7.08 (m, 2H), 7.29-7.39 (m, 4H)

Example 12

Preparation of 7-[5-(4-dimethylamino-phenyl)-4-phenyl-oxazol-2-yl]-heptanoic acid hydroxyamide 7-[5-(4-dimethylamino-phenyl)-4-phenyl-oxazol-2-yl]-heptanoic acid hydroxyamide of the following formula was prepared in the same manner as in Example 1, except for 4-dimethylaminobenzaldehyde was used as a starting material.

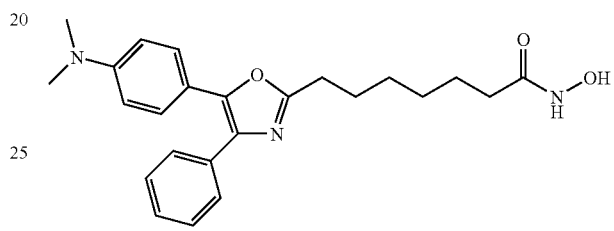

¹H-NMR (CDCl₃, 200 MHz), ppm (d): 1.21-1.58 (m, 4H), 1.59-2.01 (m, 4H), 2.01-2.43 (m, 4H), 3.62 (s, 6H), 6.76 (d, 2H), 7.15-7.65 (m, 7H)

Example 13

Preparation of 7-[4-(4-methoxy-phenyl)-5-pyridin-3-yl-oxazol-2-yl]-heptanoic acid hydroxyamide The above title compound was prepared according to the following reaction scheme 7:

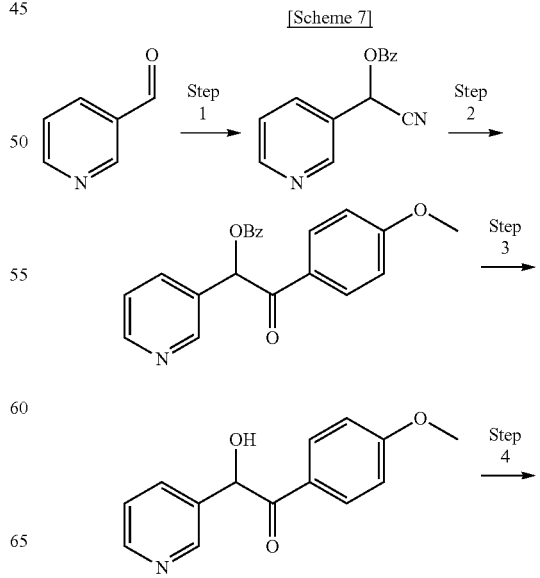

-continued

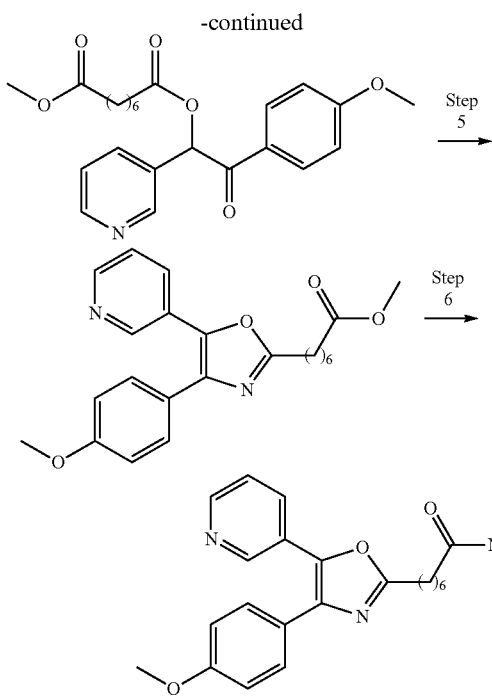

Step 1: Preparation of benzoic acid cyano-pyridin-3-yl-methyl ester

To a solution of sodium cyanide (1.96 g, 40 mmol) and benzyltridimethylammonium chloride (0.3 g, 1.3 mmol) in 7.5 mL of water was slowly added a solution of 3-pyridinecarboxaldehyde (0.88 mL, 9.3 mmol) in 15 mL of methylene chloride at 0° C. The resulting reaction solution was stirred at 0° C. for 15 min, and then benzoyl chloride (1.16 mL, 10 mmol) was additionally added thereto. After addition was complete, the reaction solution was elevated to room temperature and further stirred for 3 hours. After the reaction was complete, the reaction materials was diluted with 50 mL of ethyl acetate and 50 mL of water to dissolve salts, followed by separation of layers. The obtained organic layer was successively washed twice with 50 mL of a brine solution. The organic layer was dried over magnesium sulfate, filtered, concentrated under reduced pressure and purified by silica gel column chromatography, to give 1.95 g (yield: 95%) of benzoic acid cyano-pyridin-3-yl-methyl ester of the following formula.

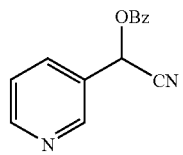

¹H-NMR (CDCl₃, 200 MHz), ppm (d): 6.75 (s, 1H), 7.44-7.54 (m, 3H), 7.63-7.71 (m, 1H), 8.00-8.11 (m, 3H), 8.76-8.78 (m, 1H), 8.90 (s, 1H)

Step 2: Preparation of benzoic acid 2-(4-methoxy-phenyl)-2-oxo-1-pyridin-3-yl-ethyl ester To a solution of sodium hydride (0.27 g, 6.72 mmol) in 10 mL of tetrahydrofuran was slowly added benzoic acid cyano-pyridin-3-yl-methyl ester (1.24 g, 5.61 mmol) prepared in Step 1 at 0° C. After addition was complete, the reaction solution was elevated to room temperature and stirred for 3 hours. Thereafter, 4-methoxybenzaldehyde (0.84 mL, 6.72 mmol) was additionally added to the resulting solution which was then stirred for 3 hours. After the reaction was complete, the reaction materials was diluted with 50 mL of ethyl acetate and 50 mL of water to dissolve salts, followed by separation of layers. The obtained organic layer was successively washed twice with 50 mL of a brine solution. The organic layer was dried over magnesium sulfate, filtered, concentrated under reduced pressure and purified by silica gel column chromatography, to give 1.21 g (yield: 60%) of benzoic acid 2-(4-methoxy-phenyl)-2-oxo-1-pyridin-3-yl-ethyl ester of the following formula.

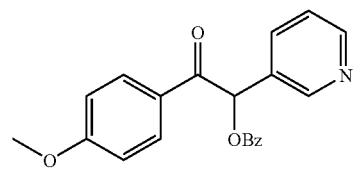

¹H-NMR (CDCl₃, 200 MHz), ppm (d): 3.77 (s, 3H), 6.91-7.01 (m, 2H), 7.42-7.53 (m, 4H), 7.82-8.01 (m, 1H), 8.09-8.18 (m, 4H), 8.69-8.77 (m, 1H), 9.20-9.22 (m, 1H)

Step 3: Preparation of 2-hydroxy-1-(4-methoxy-phenyl)-2-pyridin-3-yl-ethanone To a solution of benzoic acid 2-(4-methoxy-phenyl)-2-oxo-1-pyridin-3-yl-ethyl ester (1.21 g, 3.38 mmol) prepared in Step 2 in 3 mL of tert-butanol was slowly added 6.5 mL of 1.0 M potassium tert-butoxide under nitrogen atmosphere. The resulting mixture was stirred for 1 day and concentrated under reduced pressure to remove the solvent. The concentrate was diluted with 50 mL of ethyl acetate and 50 mL of water to dissolve salts, followed by separation of layers. The obtained organic layer was successively washed twice with 50 mL of a brine solution. The organic layer was dried over magnesium sulfate, filtered, concentrated under reduced pressure and purified by silica gel column chromatography, to give 356 mg (yield: 49%) of 2-hydroxy-1-(4-methoxy-phenyl)-2-pyridin-3-yl-ethanone of the following formula.

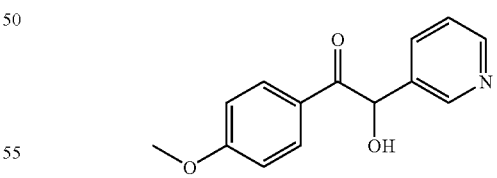

¹H-NMR (CDCl₃, 200 MHz), ppm (d): 3.79 (s, 3H), 4.77 (s, 1H), 5.94 (s, 1H), 3.66 (s, 3H), 3.77 (s, 3H), 4.08 (d, 1H), 4.73 (d, 2H), 6.78 (d, 2H), 7.02-7.09 (m, 4H), 8.34 (d, 2H)

Steps 4 through 6: Preparation of 7-[4-(4-methoxy-phenyl)-5-pyridin-3-yl-oxazol-2-yl]-heptanoic acid hydroxyamide Subsequent processes were carried out according to procedures of Steps 4 to 6 described in Example 1 and thereby 7-[4-(4-methoxy-phenyl)-5-pyridin-3-yl-oxazol-2-yl]-heptanoic acid hydroxyamide of the following formula was prepared.

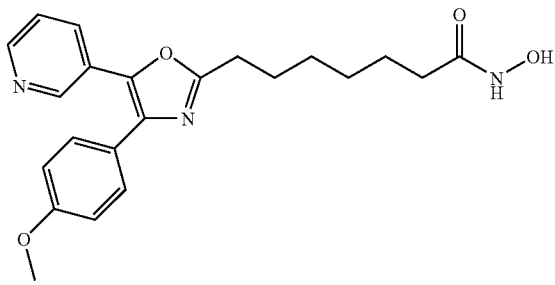

$^1$H-NMR (CDCl$_3$, 200 MHz), ppm (d): 1.24-1.38 (m, 4H), 1.43-1.92 (m, 4H), 2.06-2.11 (m, 2H), 2.84 (t, 2H), 3.83 (s, 3H), 6.92 (d, 2H), 7.27-7.31 (m, 1H), 7.51 (d, 2H), 7.83-7.87 (m, 1H), 8.49-8.52 (m, 1H), 8.82-8.83 (m, 1H), 9.81 (br s, 1H)

Using the method of Example 13, compounds of the following Examples 14 through 16 were prepared.

Example 14

Preparation of 7-[4-(4-dimethylamino-phenyl)-5-pyridin-3-yl-oxazol-2-yl]-heptanoic acid hydroxyamide 7-[4-(4-dimethylamino-phenyl)-5-pyridin-3-yl-oxazol-2-yl]-heptanoic acid hydroxyamide of the following formula was prepared in the same manner as in Example 13, except for 4-dimethylaminobenzaldehyde was used as a reactant for Step 2.

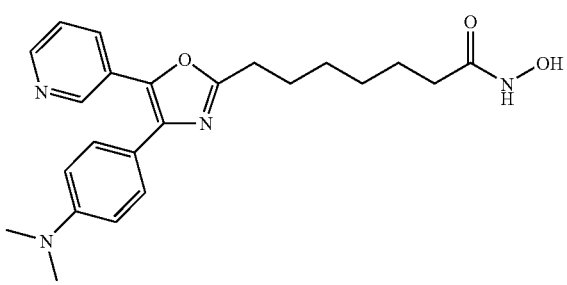

$^1$H-NMR (CDCl$_3$, 200 MHz), ppm (d): 1.28-1.40 (m, 4H), 1.42-1.88 (m, 4H), 2.30-2.42 (m, 4H), 3.69 (s, 6H), 6.76 (d, 2H), 7.50 (d, 2H), 7.95-8.00 (m, 2H), 8.51-8.55 (m, 1H), 8.82-8.90 (m, 1H)

Example 15

Preparation of 7-[4-(4-fluoro-phenyl)-5-pyridin-3-yl-oxazol-2-yl]-heptanoic acid hydroxyamide 7-[4-(4-fluoro-phenyl)-5-pyridin-3-yl-oxazol-2-yl]-heptanoic acid hydroxyamide of the following formula was prepared in the same manner as in Example 13, except for 4-fluorobenzaldehyde was used as a reactant for Step 2.

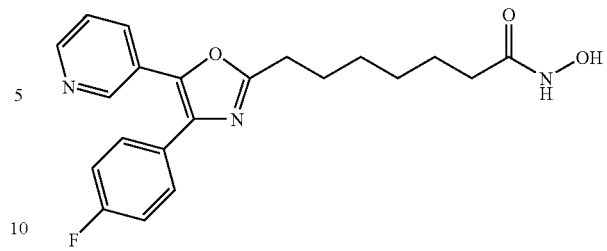

$^1$H-NMR (CDCl$_3$, 200 MHz), ppm (d): 1.24-1.31 (m, 4H), 1.59-1.98 (m, 4H), 2.01-2.14 (m, 2H), 2.79-2.98 (m, 2H), 7.06-7.14 (m, 2H), 7.29-7.39 (m, 1H), 7.41-7.59 (m, 2H), 7.83-7.87 (m, 1H), 8.56 (s, 1H), 8.83 (s, 1H)

Example 16

Preparation of 7-[4-(3-fluoro-phenyl)-5-pyridin-3-yl-oxazol-2-yl]-heptanoic acid hydroxyamide 7-[4-(3-fluoro-phenyl)-5-pyridin-3-yl-oxazol-2-yl]-heptanoic acid hydroxyamide of the following formula was prepared in the same manner as in Example 13, except for 3-fluorobenzaldehyde was used as a reactant for Step 2.

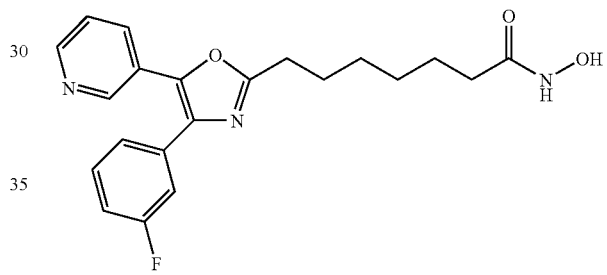

$^1$H-NMR (CDCl$_3$, 200 MHz), ppm (d): 1.24-1.41 (m, 4H), 1.59-1.98 (m, 4H), 2.01-2.13 (m, 2H), 2.82-2.98 (m, 2H), 7.06-7.18 (m, 1H), 7.29-7.37 (m, 3H), 7.46-7.62 (m, 1H), 7.84-7.88 (m, 1H), 8.56 (s, 1H), 8.84 (s, 1H)

Example 17

Preparation of 7-(4-phenyl-5-pyridin-4-yl-oxazol-2-yl)-heptanoic acid hydroxyamide The above title compound was prepared according to the following reaction scheme 8:

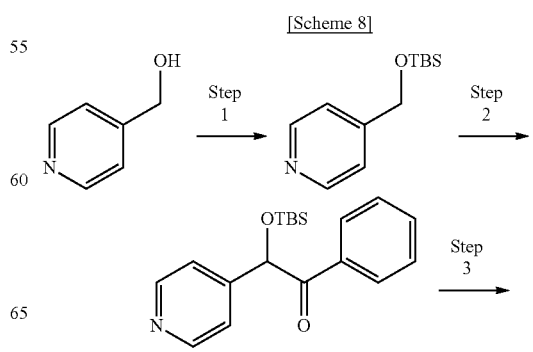

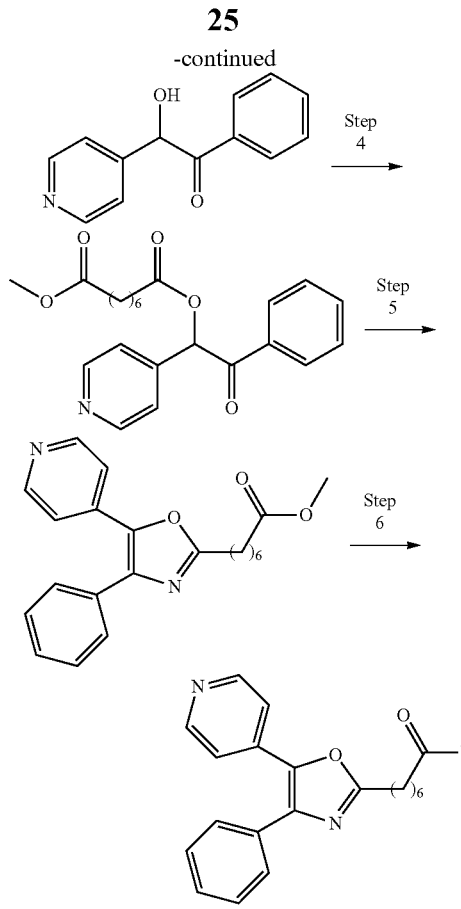

Step 1: Preparation of 4-(tert-butyl-dimethyl-silanyloxymethyl)-pyridine

To a solution of 4-pyridinecarbinol (1.09 g, 10 mmol) in 20 mL of DMF. were added tetrabutyldimethylsilyl chloride (1.81 g, 12 mmol) and imidazole (1.70 g, 25 mmol) at 0° C. After addition was complete, the reaction solution was elevated to room temperature and stirred for 1 day. After the reaction was complete, the reaction materials was diluted with 100 mL of ethyl acetate and 100 mL of water to dissolve salts, followed by separation of layers. The obtained organic layer was successively washed twice with 100 mL of a brine solution. The organic layer was dried over magnesium sulfate, filtered, concentrated under reduced pressure and purified by silica gel column chromatography, to give 1.65 g (yield: 74%) of 4-(tert-butyl-dimethyl-silanyloxymethyl)-pyridine of the following formula.

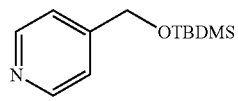

$^1$H-NMR (CDCl$_3$, 200 MHz), ppm (d): 0.13 (s, 6H), 1.98 (s, 9H), 4.77 (s, 2H), 7.26-7.29 (m, 2H), 8.55-8.58 (m, 2H)

Step 2: Preparation of 2-(tert-butyl-dimethyl-silanyloxy)-1-phenyl-2-pyridin-4-yl-ethanone To a solution of 4-(tert-butyl-dimethyl-silanyloxymethyl)-pyridine (1.12 g, 5 mmol) prepared in Step 1 in 10 mL of tetrahydrofuran was slowly added 2.63 mL of a 2.0 M lithiumdiisopropyl amide THF solution at −78° C. The resulting mixture was stirred for 1 hour and N-methoxy-N-methylbenzamide (0.87 g, 5.25 mmol) was additionally added thereto. Then, the reaction solution was stirred 0° C. for 1 hour, elevated to room temperature and stirred for 1 day. After the reaction was complete, the reaction materials were diluted with 50 mL of ethyl acetate and 50 mL of water to dissolve salts, followed by separation of layers. The obtained organic layer was successively washed twice with 50 mL of a saturated aqueous ammonium chloride solution. The organic layer was dried over magnesium sulfate, filtered and concentrated under reduced pressure to afford 0.81 g (yield: 49%) of 2-(tert-butyl-dimethyl-silanyloxy)-1-phenyl-2-pyridin-4-yl-ethanone of the following formula

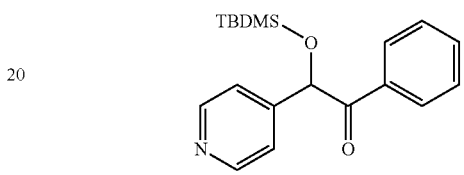

$^1$H-NMR (CDCl$_3$, 200 MHz), ppm (d): 0.01 (s, 6H), 0.92 (s, 9H), 5.68 (s, 1H), 7.29 (m, 1H), 7.38-7.42 (m, 2H), 7.48-7.52 (m, 2H), 7.96-8.01 (m, 2H), 8.59-8.62 (m, 2H)

Step 3: Preparation of 2-hydroxy-1-phenyl-2-pyridin-4-yl-ethanone

To a solution of 2-(tert-butyl-dimethyl-silanyloxy)-1-phenyl-2-pyridin-4-yl-ethanone (0.81 mg, 2.46 mmol) prepared in Step 2 in 5 mL of tetrahydrofuran was added a solution of 1.0 M tetra-n-butyl ammonium fluoride in THF (7.4 mL) and the resulting mixture was stirred for 1 hour. After the reaction was complete, the reaction materials were diluted with 50 mL of ethyl acetate and 50 mL of water to dissolve salts, followed by separation of layers. The obtained organic layer was successively washed twice with 50 mL of a brine solution. The organic layer was dried over magnesium sulfate, filtered, concentrated under reduced pressure and purified by silica gel column chromatography, to give 68 mg (yield: 13%) of 2-hydroxy-1-phenyl-2-pyridin-4-yl-ethanone of the following formula.

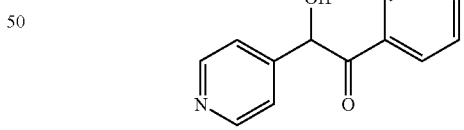

$^1$H-NMR (CDCl$_3$, 200 MHz), ppm (d): 4.65-5.28 (br s, 1H), 5.99 (s, 1H), 7.30-7.32 (m, 2H), 7.33-7.60 (m, 3H), 7.90-7.94 (m, 2H), 8.56 (d, 2H)

Steps 4 through 6: Preparation of 7-(4-phenyl-5-pyridin-4-yl-oxazol-2-yl)-heptanoic acid hydroxyamide Subsequent processes were carried out according to procedures of Steps 4 to 6 described in Example 1 and thereby 7-(4-phenyl-5-pyridin-4-yl-oxazol-2-yl)-heptanoic acid hydroxyamide of the following formula was prepared.

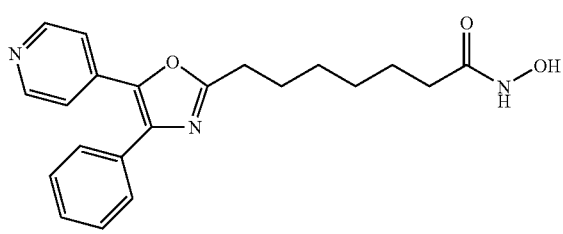

$^1$H-NMR (CDCl$_3$, 200 MHz), ppm (d): 1.28-1.41 (m, 4H), 1.66-1.98 (m, 4H), 2.07-2.15 (m, 2H), 2.82-2.86 (m, 2H), 7.18-7.59 (m, 7H), 8.55-8.57 (m, 2H)

Example 18

Preparation of 7-[5-(4-methoxy-phenyl)-4-pyridin-4-yl-oxazol-2-yl)-heptanoic acid hydroxyamide The above title compound was prepared according to the following reaction scheme 9:

[Scheme 9]

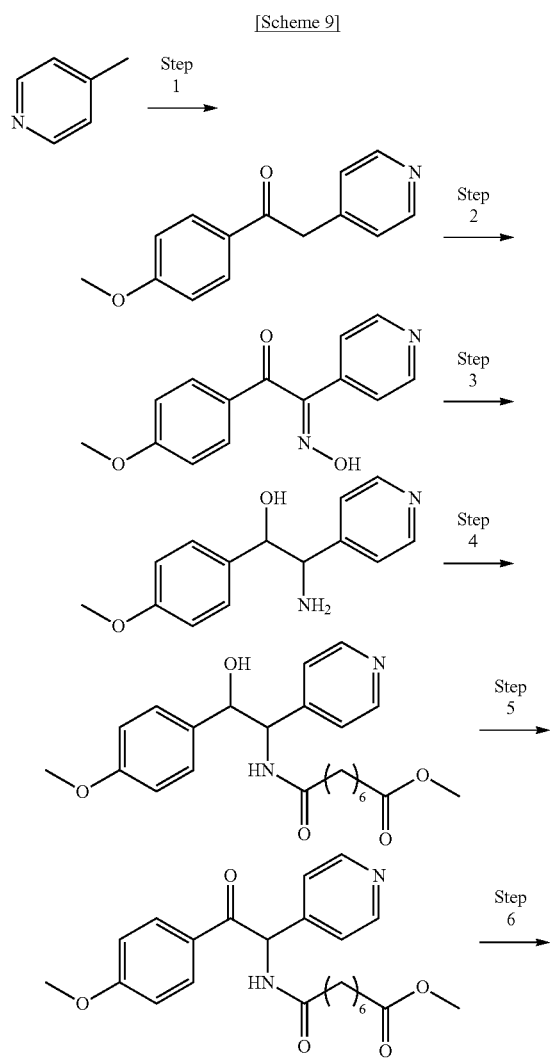

-continued

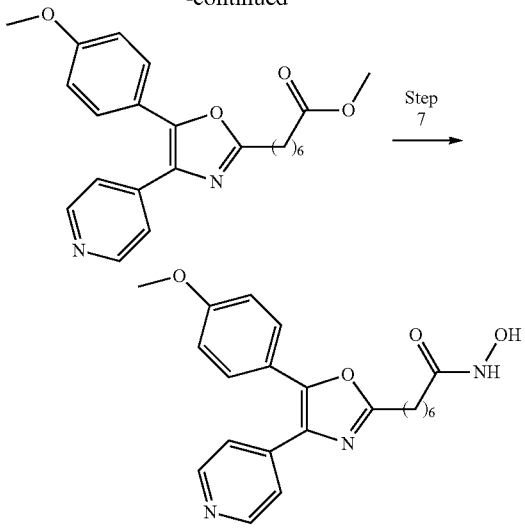

Step 1: Preparation of 1-(4-methoxy-phenyl)-2-pyridin-4-yl-ethanone

To a solution of 4-methyl-pyridine (0.49 mL, 5 mmol) and 4-N-dimethoxy-N-methyl-benzamide (0.98 g, 5 mmol) in 5 mL of THF was slowly added a solution of 1.0 M lithium bis(trimethylsilyl)amide in THF (5.5 mL) at 0° C. and the resulting mixture was stirred for 1 hour. The reaction materials were elevated to room temperature, stirred for 4 hours and 12 mL of hexane was added thereto, followed by filtration. The filtered solids were dissolved in an aqueous 2N HCl solution (7 mL) and neutralized with a saturated aqueous sodium bicarbonate solution. After neutralization was complete, the reaction materials were diluted with 50 mL of ethyl acetate and 50 mL of water to dissolve salts, followed by separation of layers. The obtained organic layer was dried over magnesium sulfate, filtered and concentrated under reduced pressure to afford 0.7 g (yield: 62%) of 1-(4-methoxy-phenyl)-2-pyridin-4-yl-ethanone of the following formula.

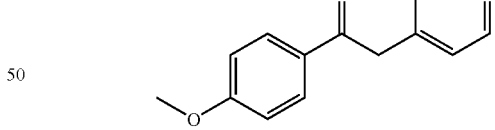

$^1$H-NMR (CDCl$_3$, 200 MHz), ppm (d): 3.90 (s, 3H), 4.26 (s, 2H), 6.95-7.00 (m, 2H), 7.21-7.26 (m, 2H), 7.98-8.02 (m, 2H), 8.56-8.59 (m, 2H)

Step 2: Preparation of 1-(4-methoxy-phenyl)-2-pyridin-4-yl-ethanone-1,2-dione-2-oxime To a solution of 1-(4-methoxy-phenyl)-2-pyridin-4-yl-ethanone (227 mg, 1 mmol) prepared in Step 1 in 3 mL of hydrogen chloride was added 3 mL of an aqueous sodium nitrite (83 mg, 1.2 mmol) solution, which was then stirred for 30 min. After the reaction was complete, an aqueous solution of 1N sodium hydroxide was added to neutralize the reaction solution, thereby forming precipitates. The thus-formed precipitates were washed several times with water and concentrated under reduced pressure to afford 190 mg (yield: 74%) of 1-(4-methoxy-phenyl)-2-pyridin-4-yl-ethanone-1,2-dione-2-oxime of the following formula.

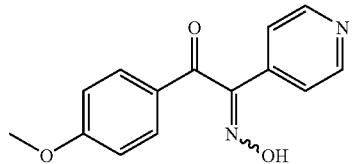

¹H-NMR (CDCl₃, 200 MHz), ppm (d): 3.81 (s, 3H), 7.06-7.09 (m, 2H), 7.36-7.39 (m, 2H), 7.76-7.80 (m, 2H), 8.57-8.59 (m, 2H), 12.27 (s, 1H)

Step 3: Preparation of 2-amino-1-(4-methoxy-phenyl)-2-pyridin-4-yl-ethanol

To a solution of 1-(4-methoxy-phenyl)-2-pyridin-4-yl-ethanone-1,2-dione-2-oxime (128 mg, 0.5 mmol) prepared in Step 2 in 1.5 mL of ethanol was added 10% palladium/charcoal (38 mg, 30 wt. %), which was then stirred under hydrogen atmosphere for 1 day. The reaction materials were filtered to remove a catalyst, and concentrated under reduced pressure to afford 50 mg (yield: 41%) of 2-amino-1-(4-methoxy-phenyl)-2-pyridin-4-yl-ethanol of the following formula.

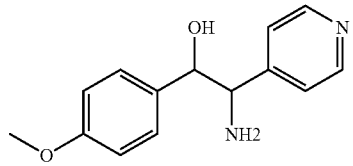

¹H-NMR (CDCl₃, 200 MHz), ppm (d): 2.75 (br s, 3H), 3.77 (s, 3H), 2.17-2.33 (m, 4H), 3.66 (s, 3H), 3.77 (s, 3H), 4.08 (d, 1H), 4.73 (d, 2H), 6.78 (d, 2H), 7.02-7.09 (m, 4H), 8.34 (d, 2H)

Step 4: Preparation of 7-[2-hydroxy-2-(4-methoxy-phenyl)-pyridin-4-yl-ethylcarbamoyl]-heptanoic acid methyl ester Using 2-amino-1-(4-methoxy-phenyl)-2-pyridin-4-yl-ethanol prepared in Step 3, 277 mg (yield: 61%) of 7-[2-hydroxy-2-(4-methoxy-phenyl)-pyridin-4-yl-ethylcarbamoyl]-heptanoic acid methyl ester of the following formula was prepared with reference to Step 4 as set forth in Example 1.

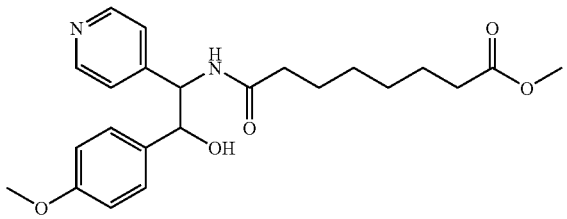

¹H-NMR (CDCl₃, 200 MHz), ppm (d): 1.27-1.30 (m, 4H), 1.45-1.71 (m, 4H), 2.17-2.33 (m, 4H), 3.66 (s, 3H), 3.77 (s, 3H), 5.03-5.14 (m, 2H), 6.72-6.82 (m, 2H), 6.91-6.95 (m, 4H), 8.28-8.31 (m, 2H)

Step 5: Preparation of 7-[2-(4-methoxy-phenyl)-2-oxo-1-pyridin-4-yl-ethyl-carbamoyl]-heptanoic acid methyl ester To a solution of dimethyl sulfoxide (0.13 mL, 1.8 mmol) and oxalyl chloride (0.13 mL, 1.44 mmol) in 1 mL of methylene chloride was added a solution of 7-[2-hydroxy-2-(4-methoxy-phenyl)-pyridin-4-yl-ethyl carbamoyl]-heptanoic acid methyl ester (297 mg, 0.72 mmol) in methylene chloride (1 mL) at −78° C., which was then stirred for 2 hours. At that temperature, triethylamine (0.3 mL, 2.16 mmol) was additionally added thereto, and the reaction materials were elevated to room temperature and were additionally stirred for 1 day. After the reaction was complete, the reaction materials were diluted with 50 mL of ethyl acetate and 50 mL of water to dissolve salts, followed by separation of layers. The obtained organic layer was successively washed twice with 50 mL of a brine solution. The organic layer was dried over magnesium sulfate, filtered, concentrated under reduced pressure and purified by silica gel column chromatography to afford 218 mg (yield: 74%) of 7-[2-(4-methoxy-phenyl)-2-oxo-1-pyridin-4-yl-ethylcarbanoyl]-heptanoic acid methyl ester of the following formula.

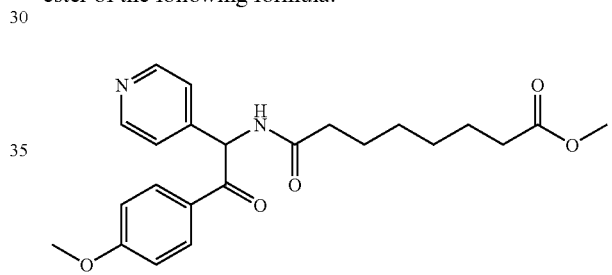

¹H-NMR (CDCl₃, 200 MHz), ppm (d): 1.28-1.41 (m, 4H), 1.58-1.79 (m, 4H), 2.23-2.32 (m, 4H), 3.68 (s, 3H), 3.85 (s, 3H), 6.48-6.52 (m, 1H), 6.89-6.93 (m, 2H), 7.28-7.33 (m, 2H), 7.93-7.97 (m, 2H), 8.53-8.56 (m, 2H)

Step 6: Preparation of 7-[5-(4-methoxy-phenyl)-4-pyridin-4-yl-oxazol-2-yl)-heptanoic acid methyl ester Triphenyl phosphine (278 mg, 1.06 mmol), iodine (269 mg, 1.06 mmol) and triethylamine (0.3 mL, 2.12 mmol) were added at 0° C. to a solution in which 7-[2-(4-methoxy-phenyl)-2-oxo-1-pyridin-4-yl-ethylcarbamoyl]-heptanoic acid methyl ester (218 mg, 0.53 mmol) prepared in Step 5 was dissolved in 1.5 mL of methylene chloride, and the resulting mixture was stirred for 30 min. The reaction materials were elevated to room temperature and were further stirred for 1 day. After the reaction was complete, the reaction materials were diluted with 50 mL of ethyl acetate and 50 mL of water to dissolve salts, followed by separation of layers. The obtained organic layer was successively washed twice with 50 mL of a brine solution. The organic layer was dried over magnesium sulfate, filtered, concentrated under reduced pressure and purified by silica gel column chromatography to afford 7-[5-(4-methoxy-phenyl)-4-pyridin-4-yl-oxazol-2-yl)-heptanoic acid methyl ester of the following formula.

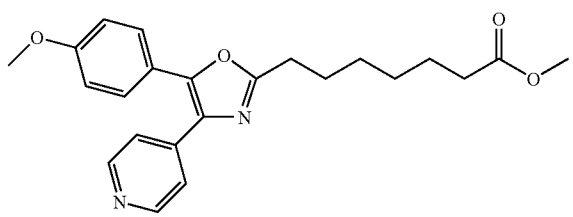

¹H-NMR (CDCl₃, 200 MHz), ppm (d): 1.38-1.60 (m, 4H), 1.61-1.69 (m, 2H), 1.80-1.88 (m, 2H), 2.31 (t, 2H), 2.82 (t, 2H), 3.64 (s, 3H), 3.83 (s, 3H), 6.91-6.99 (m, 2H), 7.38-7.72 (m, 4H), 8.54-8.57 (m, 2H)

Step 7: Preparation of 7-[5-(4-methoxy-phenyl)-4-pyridin-4-yl-oxazol-2-yl)-heptanoic acid hydroxyamide Subsequent processes were carried out according to a procedure of Step 6 described in Example 1 and thereby 53 mg of 7-[5-(4-methoxy-phenyl)-4-pyridin-4-yl-oxazol-2-yl)-heptanoic acid hydroxyamide (yield: 25%) was prepared.

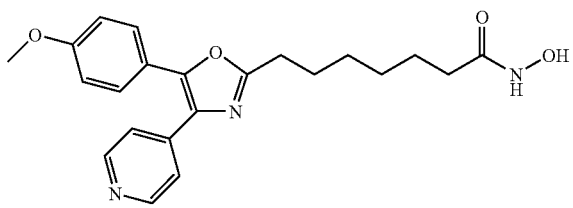

¹H-NMR (CDCl₃, 200 MHz), ppm (d): 1.28-1.41 (m, 4H), 1.67-1.83 (m, 4H), 2.11-2.15 (m, 2H), 2.83-2.86 (m, 2H), 3.87 (s, 3H), 6.95 (d, 2H), 7.49 (d, 2H), 7.58 (d, 2H), 8.56 (d, 2H)

Example 19

Preparation of 7-[5-(4-ethoxy-phenyl)-4-pyridin-4-yl-oxazol-2-yl]-heptanoic acid hydroxyamide 7-[5-(4-ethoxy-phenyl)-4-pyridin yl-oxazol-2-yl]-heptanoic acid hydroxyamide of the following formula was prepared in the same manner as in Example 18, except for 4-ethoxy-N-methylbenzamide was used as a starting material.

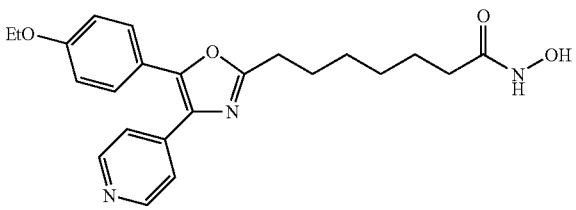

¹H-NMR (CDCl₃, 200 MHz), ppm (d): 1.28-1.50 (m, 7H), 1.63-1.83 (m, 4H), 2.11-2.15 (m, 2H), 2.79-2.86 (m, 2H), 4.07 (t, 2H), 6.95 (d, 2H), 7.49 (d, 2H), 7.58 (d, 2H), 8.56 (d, 2H)

Example 20

Preparation of 7-[5-(4-hydroxy-phenyl)-4-phenyl-oxazol-2-yl]-heptanoic acid hydroxyamide The above title compound was prepared according to the following reaction scheme 10:

[Scheme 10]

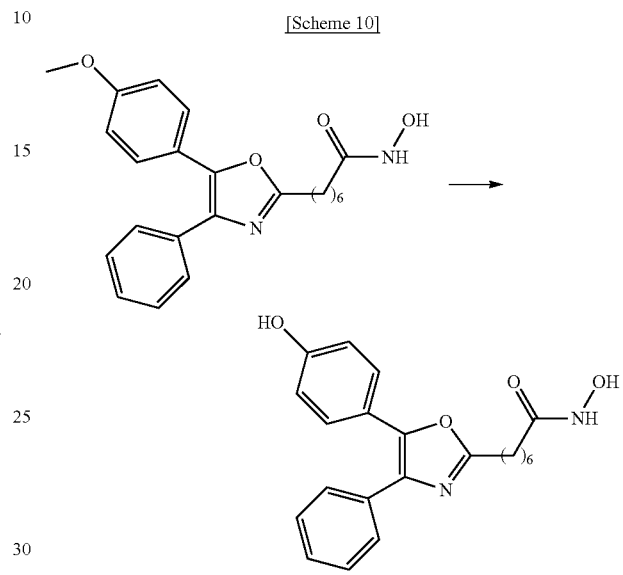

A solution (0.11 mL) of 1.0 M tribromoborane was added at −78° C. to a solution in which 7-(5-4-methoxyphenyl)-4-phenyloxazol-2-yl)heptanoic acid hydroxyamide (19.7 mg, 0.05 mmol) prepared in Example 1 was dissolved in 0.2 mL of methylene chloride, which was then stirred for 1.5 hours. The reaction was elevated to 0° C., stirred for additional 1 hour, and was terminated with addition of 2 mL of water. An aqueous solution of 1N NaOH was slowly added to the reaction liquid which was then stirred and neutralized with addition of an aqueous solution of 1N HCl. After neutralization was complete, 10 mL of ethyl acetate was added to separate an organic layer and aqueous layer, and the obtained organic layer was successively washed twice with 10 mL of a brine solution. The organic layer was dried over magnesium sulfate, filtered, concentrated under reduced pressure and purified a product which was then separated by silica gel column chromatography to afford 10 mg (yield: 53%) of a tide compound.

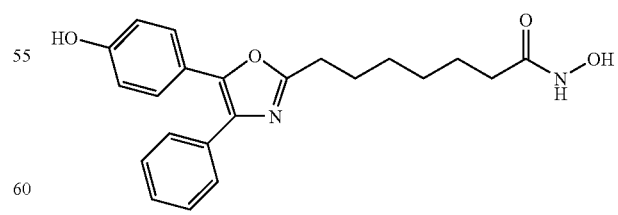

¹H-NMR (CD₃OD, 500 MHz), ppm (d): 1.40-1.46 (m, 4H), 1.63-1.66 (m, 2H), 1.83-1.85 (M, 2H), 2.09 (t, 2H), 2.84 (t, 2H), 6.78 (d, 2H), 7.32-7.53 (m, 5H), 7.54 (d, 2H)

For compounds of the present invention synthesized in the above-mentioned Examples 1 through 20, tests on HDAC-inhibiting activity and in vitro toxicity were carried out according to the following methods.

Experimental Example 1

Inhibition of HDAC Activity

In order to determine inhibitory activity of a compound in accordance with the present invention on HDAC, evaluation was carried out using an aminocoumarin derivative of ω-acetylated lysine as a substrate for an enzyme. As an enzyme source, a nuclear extract obtained from human cervical cancer cell line HeLa cells was used. The above evaluation was carried out with modification of a method based on the details described in Weegener et al. (2003) Analytical Biochemistry, 321, 203-208. That is, 75 mM substrate, 10 mg of nuclear extract and a compound of Example 1 at different concentrations were added and maintained at room temperature for 30 min. Trypsin (10 mg/ml) and Trichostatin A (final concentration: 2 mM) were added to the resulting mixture which was reacted at the same temperature for 20 min, thereby terminating the reaction. The enzyme activity-inhibitory concentration of the compound added was determined using a fluorometer. As a control compound, suberoylanilide hydroxamic acid (SAHA) was used. IC50 in Table 1 below refers to a concentration of the compound that leads to a 50% decrease in activity of HDAC. As shown in Table 1, it can be seen that the compound of the present invention exerts superior inhibitory effects on activity of HDAC with use of a lower concentration thereof.

Experimental Example 2

Assay for In Vitro Toxicity

In order to determine in vitro toxicity of a compound in accordance with the present invention, 18 species of human cancer cell lines (HeLa, cervical cancer cell line; HCT116, SW480, SW620, RKO, colon cancer cell lines; H460, H1299, A549, lung cancer cell lines; MCF7, MDA-MB231, MDA-MB453, breast cancer cell lines; Jurkat, K562, THP1, Ramos, U937, blood cancer cell lines; PC3, DU145, prostate cancer cell lines) were used. Cell lines were cultured in RPMI 1640 culture medium containing penicillin/streptomycin (100 units/mL) and heat-inactivated 5% fetal bovine serum (FBS) under standard culture conditions (95% $O_2$, 5% $CO_2$, and 100% relative humidity). Thereafter, single cell suspension was obtained via trypsin treatment and pipetting. The suspension was diluted with the same medium such that a cell density is in a range of $8\times10^3$ to $1.5\times10^4$ cells/well, and was transferred to a 96-well microtiter plate. After culturing for 24 hours, cell cultures were treated with respective compounds of Examples at various concentrations. Following 48 hr-cultivation, inhibition of cell proliferation and in vitro toxicity were measured using a CellTiter-Glo® Luminescent Cell Viability Assay Kit (Promega, USA). The above evaluation was carried out according to the methods given in a manufacture's manual. GI50 in Table 1 below refers to a concentration that compounds of Examples cause 50% growth inhibition of various cancer cells.

TABLE 1

| Example No. | Structure | HDAC IC50 (nM) | Solubility mg/ml | GI50 (μm) | | | |
|---|---|---|---|---|---|---|---|
| | | | | HeLa | HCT116 | H460 | MCF7 |
| 1 | 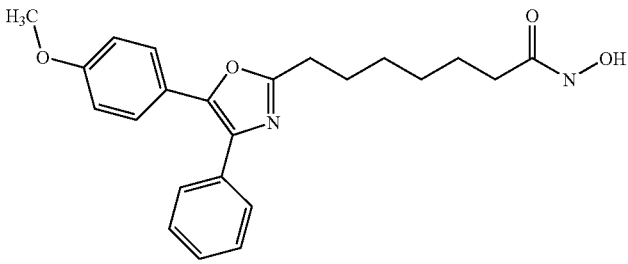 | 1.07 | 0.2 | 1.4 | 3 | 3.63 | 0.7 |
| 2 | 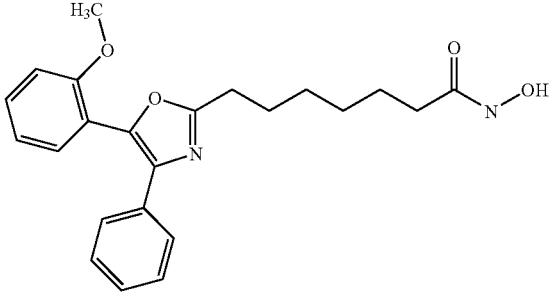 | 6.61 | 0.4 | 9.33 | 8.3 | n.a | n.a |

TABLE 1-continued
| Example No. | Structure | HDAC IC50 (nM) | Solubility mg/ml | GI50 (μm) HeLa | HCT116 | H460 | MCF7 |
|---|---|---|---|---|---|---|---|
| 3 | 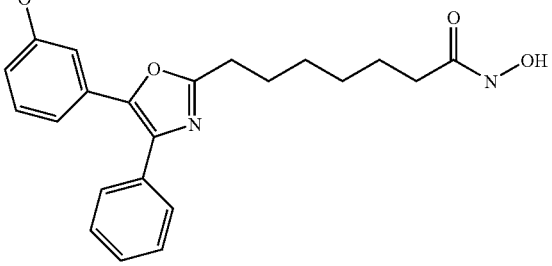 | 1.58 | 0.2 | 16.9 | 6.5 | n.a | n.a |
| 4 | 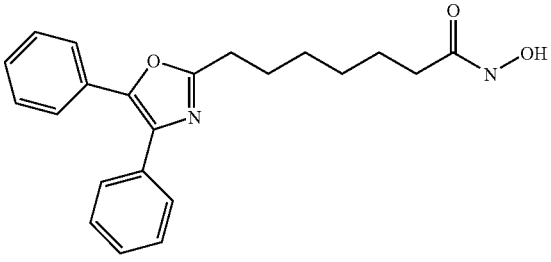 | 2 | 0.2 | 2.5 | 3.5 | n.a | 6.6 |
| 5 | 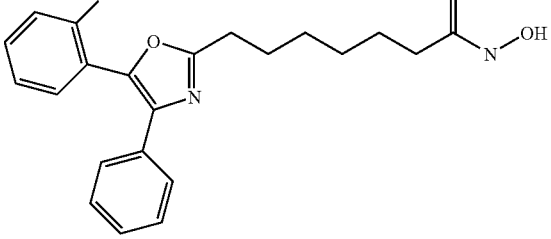 | 1.74 | 0.3 | 3.6 | 10.7 | 14.2 | n.a |
| 6 | 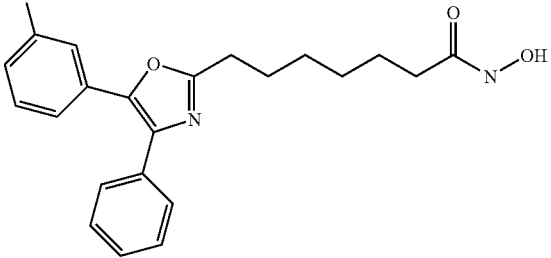 | 1.48 | 0.4 | 10.7 | 9.5 | 15.8 | 3.8 |
| 7 | 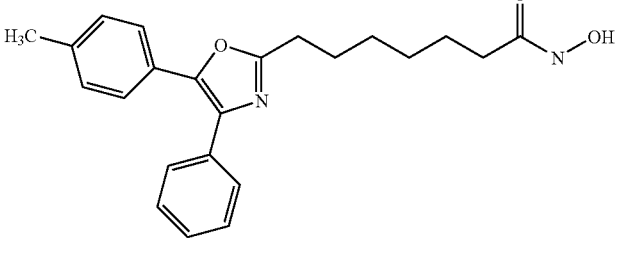 | 2 | 0.2 | 2.4 | 2.7 | 9.9 | n.a |

TABLE 1-continued

| Example No. | Structure | HDAC IC50 (nM) | Solubility mg/ml | GI50 (μm) HeLa | HCT116 | H460 | MCF7 |
|---|---|---|---|---|---|---|---|
| 8 | EtO-phenyl-oxazole(phenyl)-(CH2)6-C(O)NHOH | 1.2 | 0.2 | 1.5 | 1.2 | 4.2 | n.a |
| 9 | F-phenyl-oxazole(phenyl)-(CH2)6-C(O)NHOH | 4.97 | 0. | 14.2 | 5.9 | 19.1 | n.a |
| 10 | MeO-phenyl-oxazole(4-MeO-phenyl)-(CH2)6-C(O)NHOH | 0.47 | 0.2 | 3 | 2.4 | 9.2 | 0.8 |
| 11 | MeO-phenyl-oxazole(2-OMe-phenyl)-(CH2)6-C(O)NHOH | 7.24 | 0.4 | 1.2 | 2.4 | 10.2 | n.a |
| 12 | Me2N-phenyl-oxazole(phenyl)-(CH2)6-C(O)NHOH | 5.01 | 0.7 | 14.1 | 9.8 | 19.5 | 6.9 |

TABLE 1-continued

| Example No. | Structure | HDAC IC50 (nM) | Solubility mg/ml | GI50 (μm) | | | |
|---|---|---|---|---|---|---|---|
| | | | | HeLa | HCT116 | H460 | MCF7 |
| 13 | 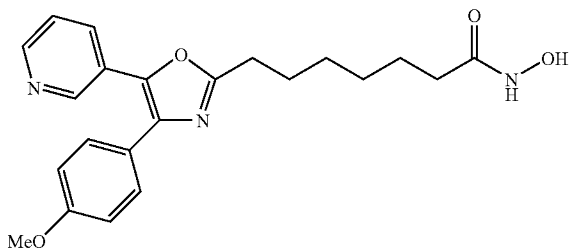 | 14.5 | 0.9 | 3.9 | 3.9 | 4.4 | 1 |
| 14 | 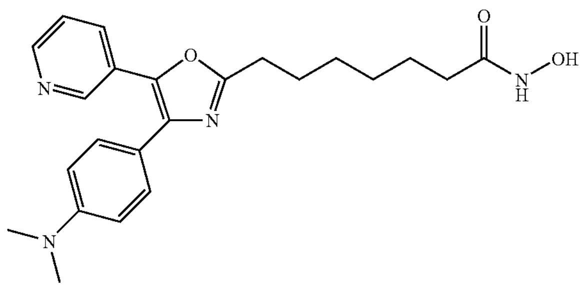 | 2.95 | 1.0 | 7.8 | 8.7 | 23.5 | 8.7 |
| 15 | 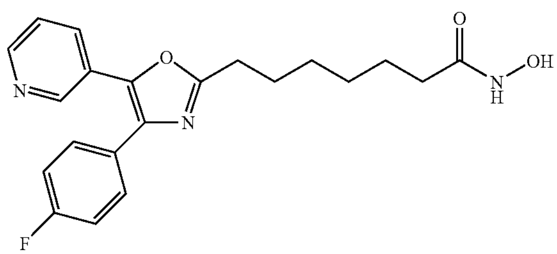 | 38.4 | 2.0 | 30.1 | n.a | 69 | n.a |
| 16 | 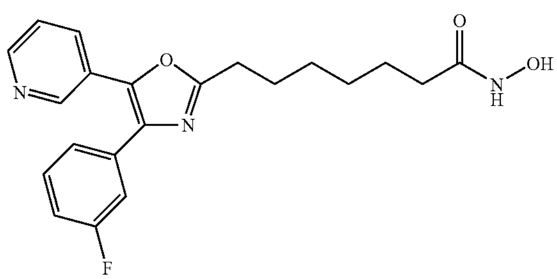 | 32.3 | 1.4 | 20.7 | n.a | 52.3 | n.a |
| 17 | 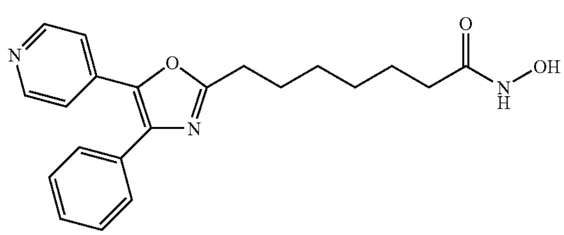 | 19.5 | 0.9 | 3.5 | 5.4 | 7.3 | 1.8 |
| 18 | 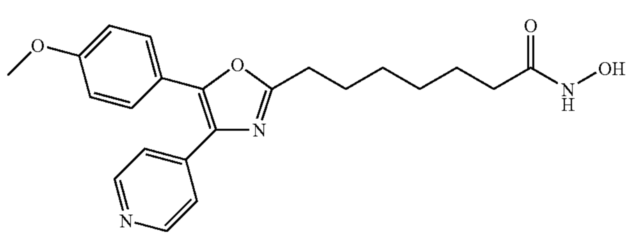 | 14.0 | 0.9 | 9.1 | 3.8 | 11.7 | n.a |

TABLE 1-continued

| Example No. | Structure | HDAC IC50 (nM) | Solubility mg/ml | GI50 (μm) HeLa | HCT116 | H460 | MCF7 |
|---|---|---|---|---|---|---|---|
| 19 | [structure: EtO-phenyl-oxazole-pyridinyl-hexanoic acid hydroxamide] | 0.68 | 0.7 | 2.9 | 4.0 | 4.1 | 1.1 |
| 20 | [structure: HO-phenyl-oxazole-phenyl-hexanoic acid hydroxamide] | 1.7 | 0.3 | 2.4 | 1.5 | 5.4 | n.a |

Experimental Example 3

In Vitro Activity Inhibition of Histone Deacetylase

Human color cancer cell line (HCT116) was cultured in RPMI 1640 culture medium containing penicillin/streptomycin (100 units/mL) and heat-inactivated 5% fetal bovine serum (FBS) under standard culture conditions (95% $O_2$, 5% $CO_2$, 37° C., and 100% relative humidity). Test compounds were dissolved in dimethylsulfoxide (DMSO) and were used as a final concentration of 1 μM. Cells ($3 \times 10^7$) were cultured in the presence of the test compound (1 μM, Example 1) and absence thereof for 0, 2 and 5 hours, respectively. The cell suspension, which was obtained via trypsin treatment and pipetting, was centrifuged at 200×g for 10 min to form a pellet. The thus-formed pellet was washed twice with 10-fold volume of saline and re-suspended in a buffer [10 nM HEPES, pH 7.9, 1.5 mM $MgCl_2$, 10 mM KCl, 0.5 mM DTT, 1.5 mM PMSF]. Thereafter, hydrochloric acid was added in a final concentration of 0.2 M to the resulting suspension which was then stored on ice for 30 min. The final suspension was centrifuged at 11,000 rpm and 4° C. for 10 min. The supernatant was subjected to dialysis against 0.1M acetic acid at 4° C., twice, each for 2 hours, followed by dialysis against saline at 4° C. for 1, 3 and 12 hours or more.

Dialyzed proteins were subjected to gel electrophoresis using 16% protein gel and were probed with acetylated histone H3 (Ac-H3) or H4 (Ac-H4) antibodies (Upstate Biotechnology Inc). Probing was carried out using a chemiluminescence system (ECL, Amersham). In order to compare the equal amount of proteins, protein quantification and protein gel were run in parallel, followed by coumassie blue staining. The results thus obtained are shown in FIG. 1. As can be seen from FIG. 1, a degree of acetylation for histone H3 (Ac-H3) and H4 (Ac-H4) acetylated over time was confirmed via Western blot analysis.

Experimental Example 4

In Vivo Pre-Toxicity

In order to confirm acute toxicity in vivo, a Rotarod Neurotoxicity test was carried out on ICR-BG mice (N=8). Animals were administered at a dose of 300 mg/kg. Animals received training at 7 rpm for 10 min twice, and 1 hour later the compound of Example 1 was administered intraperitoneally (ip) to 8 mice. Thereafter, for one minute at the intervals of every 30 min, 1 hour, 2 hours and 4 hours, times that animals fell from the rotarod and death of animal post-drug administration or affliction-related responses were continuously observed. When mice fell from the rotarod more than thrice in one minute, it was regarded as fall off. The results thus obtained are shown in Table 2 below.

TABLE 2

| No. | Weight (g) | 0.5 h | 1 hr | 2 hr | 4 hr |
|---|---|---|---|---|---|
| N = 8 | 25-27(average 26) | 1/8(Fallen off) | 1/8 | 0/8 | 0/8 |

As shown in Table 2, it can be seen that essentially none of 8 mice fell off the rotarod during experiments after administration of the compound in accordance with the present invention. In addition, no death of animals or no response related to affliction was observed.

Therefore, it can be seen that the HDAC-inhibiting compound in accordance with the present invention exhibits high-inhibitory effects on HDAC activity even at a lower concentration, specifically inhibits growth of cancer cells and further does not produce acute toxicity in vivo. Consequently, the compound in accordance with the present invention is an HDAC inhibitor, is a selective inhibitor against growth of cancer cells and thereby can be used for preparation of an anti-cancer composition having superior efficacy.

Experimental Example 5

Inhibition of Extracellular LPS-Induced No Increases

As one of the methods to confirm anti-inflammatory responses, inhibition of increases in nitric oxide (NO) due to lipopolysaccharide (LPS) was carried out. Mouse cell line (Raw cell) was cultured in RPMI 1640 culture medium containing penicillin/streptomycin (100 units/mL) and heat-inactivated 5% fetal bovine serum (FBS) under standard culture conditions (95% $O_2$, 5% $CO_2$, 37° C., and 100% relative humidity). Test compounds were dissolved in dimethylsulfoxide (DMSO) and were used as a final concentration of 1 to 40 µM. Cells were proliferated to a cell density of $5×10^3$ to $2×10^4$ cells on a 24-well plate and were treated with the respective compounds (equal amounts of 5 µM) 1 hour prior to treatment with LPS (10 µM/ml). The thus-treated cells were cultured for 18 hours, and thereafter the amounts of NO thus produced were measured using Griess Reagent. Measurement was confirmed using an absorption spectrophotometer at 540 nm. The value was expressed as percentage (%) relative to a control in which LPS alone was treated.

TABLE 3

Inhibition of LPS-induced NO increases

| Con. (5 µM) | NO (µM/L) | % (vs LPS) |
| --- | --- | --- |
| LPS control | 78.7 | 100 |
| Example 1 | 63.7 | 57.9 |
| Example 2 | 77.9 | 97.8 |
| Example 5 | 69.0 | 72.7 |
| Example 6 | 70.6 | 77.1 |
| Example 8 | 63.7 | 57.7 |
| Example 9 | 71.4 | 79.4 |
| Example 11 | 65.0 | 61.3 |
| Example 12 | 72.9 | 83.7 |
| Example 13 | 57.1 | 39.2 |
| Example 14 | 69.6 | 74.4 |
| Example 15 | 66.6 | 65.8 |
| Example 16 | 63.0 | 55.7 |
| Example 17 | 59.6 | 46.1 |
| Example 18 | 68.6 | 71.6 |
| Example 20 | 55.9 | 35.9 |

Experimental Example 6

Radio-Sensitizing Effects

In order to confirm whether the compound synthesized according to the present invention further improves anti-cancer effects in conjunction with radiation, an experiment was carried out using a human cervical cancer cell line (HeLa). Cells were cultured in RPMI 1640 culture medium containing penicillin/streptomycin (100 units/mL) and heat-inactivated 5% fetal bovine serum (FBS) under standard culture conditions (95% $O_2$, 5% $CO_2$, 37° C., and 100% relative humidity). It can be seen that, as compared to the group which was treated with the compound of Example 1 alone (8 µM) or the group which was treated with radiation (4 Gy) alone, combined treatment of the compound of Example 1 and radiation has resulted in 3 to 5 times higher anticancer activity (see FIGS. 2 and 3). FIG. 2 is a graph showing increases in numbers of apoptotic cells upon simultaneous treatment of the compound of the present invention in conjunction with radiation and FIG. 3 is a graph showing improved inhibition on colony-forming ability of tumor cells, via a clonogenic assay, upon simultaneous treatment of the compound in accordance with the present invention with radiation. Apoptosis was assayed using CellTiter-Glo® Luminescent Cell Viability Assay Kit (Promega, USA). The above evaluation was carried out according to the methods given in a manufacture's manual. In conclusion, combined application of the compound of the present invention in conjunction with radiation for anti-cancer therapy leads to increased anti-cancer activity.

INDUSTRIAL APPLICABILITY

In accordance with the present invention, provided are an oxazole hydroxamic acid derivative and a pharmaceutically useful salt thereof, which are capable of treating and/or preventing various diseases, resulting from abnormal expression by histone deacetylase. Such compounds exhibit, at a low concentration, high inhibitory effects of HDAC activity and specifically inhibit growth of cancer cells. In addition, there is provided a compound that is effective as a sensitizing agent capable of enhancing therapeutic effects while minimizing adverse side effects due to radiation in conventional radiotherapies, and is also effective as an anti-inflammatory agent.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An oxazole hydroxamic acid derivative selected from the group consisting of 7-(5-(4-methoxy-phenyl)-4-phenyl-oxazol-2-yl)-heptanoic acid hydroxyamide, 7-[5-(2-methoxy-phenyl)-4-phenyl-oxazol-2-yl-heptanoic acid hydroxyamide, 7-[5-(3-methoxy-phenyl)-4-phenyl-oxazol-2-yl-heptanoic acid hydroxyamide, 7-[5-(2-fluoro-phenyl)-4-phenyl-oxazol-2-yl]-heptanoic acid hydroxyamide, 7-[5-(3-fluoro-phenyl)-4-phenyl-oxazol-2-yl]-heptanoic acid hydroxyamide, 7-(4-phenyl-5-p-tolyl-oxazol-2-yl)-heptanoic acid hydroxyamide, 7-[5-(4-ethoxy-phenyl)-4-phenyl-oxazol-2-yl]-heptanoic acid hydroxyamide, 7-[5-(4-fluoro-phenyl)-4-phenyl-oxazol-2-yl]-heptanoic acid hydroxyamide, 7-[4,5-bis-(4-methoxy-phenyl)-oxazol-2-yl]-heptanoic acid hydroxyamide, 7-[4-(2-methoxy-phenyl)-5-(4-methoxy-phenyl)-oxazol-2-yl]-heptanoic acid hydroxyamide, 7-[5-(4-dimethylamino-phenyl)-4-phenyl-oxazol-2-yl]-haptanoic acid hydroxyamide, acid hydroxyamide, 7-[4-(4-methoxy-phenyl)-5-pyridin-3-yl-oxazol-2-yl]-heptanoic acid hydroxyamide, 7-[4-(4-dimethylamino-phenyl)-5-pyridin-3-yl-oxazol-2-yl]-heptanoic acid hydroxyamide, 7-[4-(4-fluoro-phenyl)-5-pyridin-3-yl-oxazol-2-yl]-heptanoic acid hydroxyamide, 7-[4-(3-fluoro-phenyl)-5-pyridin-3-yl-oxazol-2-yl]-heptanoic acid hydroxyamide, 7-(4-phenyl-5-pyridin-4-yl-oxazol-2-yl)-heptanoic acid hydroxyamide, 7-[5-(4-methoxy-phenyl)-4-pyridin-4-yl-oxazol-2-yl)heptanoic acid hydroxyamide, 7-[5-(4-ethoxy-phenyl)-4-pyridin yl-oxazol-2-yl)-heptanoic acid hydroxyamide and 7-[5-(4-hydroxy-phenyl)-4-phenyl-oxazol-2-yl]-heptanoic acid hydroxyamide; or a pharmaceutically useful salt thereof.

2. A pharmaceutical composition comprising an oxazole hydroxamic acid derivative selected from the group consisting of 7-(5-(4-methoxy-phenyl)-4-phenyl-oxazol-2-yl)-heptanoic acid hydroxyamide, 7-[5-(2-methoxy-phenyl)-4-phenyl-oxazol-2-yl-heptanoic acid hydroxyamide, 7-[5-(3-methoxy-phenyl)-4-phenyl-oxazol-2-yl-heptanoic acid hydroxyamide, 7-[5-(2-fluoro-phenyl)-4-phenyl-oxazol-2-yl]-heptanoic acid hydroxyamide, 7-[5-(3-fluoro-phenyl)-4- phenyl-oxazol-2-yl]-heptanoic acid hydroxyamide, 7-(4-phenyl-5-p-tolyl-oxazol-2-yl)-heptanoic acid hydroxyamide, 7-[5-(4-ethoxy-phenyl)-4-phenyl-oxazol-2-yl]-heptanoic acid hydroxyamide, 7-[5-(4-fluoro-phenyl)-4-phenyl-oxazol-2-yl]-heptanoic acid hydroxyamide, 7-[4,5-bis-(4-methoxy-phenyl)-oxazol-2-yl]-heptanoic acid hydroxyamide, 7-[4-(2-methoxy-phenyl)-5-(4-methoxy-phenyl)-oxazol-2-yl]-heptanoic acid hydroxyamide, 7-[5-(4-dimethylamino-phenyl)-4-phenyl-oxazol-2-yl]-heptanoic acid hydroxyamide, 7-[4-(4-methoxy-phenyl)-5-pyridin-3-yl-oxazol-2-yl]-heptanoic acid hydroxyamide, 7-[4-(4-dimethylamino-phenyl)-5-pyridin-3-yl-oxazol-2-yl]-heptanoic acid hydroxyamide, 7-[4-(4-fluoro-phenyl)-5-pyridin-3-yl-oxazol-2-yl]-heptanoic acid hydroxyamide, 7-[4-(3-fluoro-phenyl)-5-pyridin-3-yl-oxazol-2-yl]-heptanoic acid hydroxyamide, 7-(4-phenyl-5-pyridin-4-yl-oxazol-2-yl)-heptanoic acid hydroxyamide, 7-[5-(4-methoxy-phenyl)-4-pyridin-4-yl-oxazol-2-yl)-heptanoic acid hydroxyamide, 7-[5-(4-ethoxy-phenyl)-4-pyridin-4-yl-oxazol-2-yl)-heptanoic acid hydroxyamide and 7-[5-(4-hydroxy-phenyl)-4-phenyl-oxazol-2-yl]-heptanoic acid hydroxyamide.

3. A histone decarboxylase inhibitor comprising an oxazole hydroxamic acid derivative selected from the group consisting of 7-(5-(4-methoxy-phenyl)-4-phenyl-oxazol-2-yl)-heptanoic acid hydroxyamide, 7-[5-(2-methoxy-phenyl)-4-phenyl-oxazol-2-yl-heptanoic acid hydroxyamide, 7-[5-(3-methoxy-phenyl)-4-phenyl-oxazol-2-yl-heptanoic acid hydroxyamide, 7-[5-(2-fluoro-phenyl)-4-phenyl-oxazol-2-yl]-heptanoic acid hydroxyamide, 7-[5-(3-fluoro-phenyl)-4-phenyl-oxazol-2-yl]-heptanoic acid hydroxyamide, 7-(4-phenyl-5-p-tolyl-oxazol-2-yl)-heptanoic acid hydroxyamide, 7-[5-(4-ethoxy-phenyl)-4-phenyl-oxazol-2-yl]-heptanoic acid hydroxyamide, 7-[5-(4-fluoro-phenyl)-4-phenyl-oxazol-2-yl]-heptanoic acid hydroxyamide, 7-[4,5-bis-(4-methoxy-phenyl)-oxazol-2-yl]-heptanoic acid hydroxyamide, 7-[4-(2-methoxy-phenyl)-5-(4-methoxy-phenyl)-oxazol-2-yl]-heptanoic acid hydroxyamide, 7-[5-(4-dimethylamino-phenyl)-4-phenyl-oxazol-2-yl]-heptanoic acid hydroxyamide, 7-[4-(4-methoxy-phenyl)-5-pyridin-3-yl-oxazol-2-yl]-heptanoic acid hydroxyamide, 7-[4-(4-dimethylamino-phenyl)-5-pyridin-3-yl-oxazol-2-yl]-heptanoic acid hydroxyamide, 7-[4-(4-fluoro-phenyl)-5-pyridin-3-yl-oxazol-2-yl]-heptanoic acid hydroxyamide, 7-[4-(3-fluoro-phenyl)-5-pyridin-3-yl-oxazol-2-yl]-heptanoic acid hydroxyamide, 7-(4-phenyl-5-pyridin-4-yl-oxazol-2-yl)-heptanoic acid hydroxyamide, 7-[5-(4-methoxy-phenyl)-4-pyridin-4-yl-oxazol-2-yl)-heptanoic acid hydroxyamide, 7-[5-(4-ethoxy-phenyl)-4-pyridin-4-yl-oxazol-2-yl)-heptanoic acid hydroxyamide and 7-[5-(4-hydroxy-phenyl)-4-phenyl-oxazol-2-yl]-heptanoic acid hydroxyamide.

4. The inhibitor according to claim 3, wherein the inhibitor is an anticancer agent for cervical cancer, colon cancer, breast cancer, blood cancer and prostate cancer or an anti-inflammatory agent.

* * * * *